(12) United States Patent
Himmelsbach et al.

(10) Patent No.: US 10,053,471 B2
(45) Date of Patent: Aug. 21, 2018

(54) AZABENZIMIDAZOLE DERIVATIVES

(71) Applicant: Boehringer Ingelheim International GmbH, Ingelheim am Rhein (DE)

(72) Inventors: Frank Himmelsbach, Mittelbiberach (DE); Elke Langkopf, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/543,242

(22) PCT Filed: Jan. 13, 2016

(86) PCT No.: PCT/EP2016/050557
§ 371 (c)(1),
(2) Date: Jul. 13, 2017

(87) PCT Pub. No.: WO2016/113299
PCT Pub. Date: Jul. 21, 2016

(65) Prior Publication Data
US 2018/0002349 A1 Jan. 4, 2018

(30) Foreign Application Priority Data

Jan. 16, 2015 (EP) .................................... 15151419
May 11, 2015 (EP) .................................... 15167116

(51) Int. Cl.
*C07D 401/14* (2006.01)
*A61K 31/437* (2006.01)
*C07D 519/00* (2006.01)
*A61K 45/06* (2006.01)

(52) U.S. Cl.
CPC .......... *C07D 519/00* (2013.01); *A61K 31/437* (2013.01); *A61K 45/06* (2013.01)

(58) Field of Classification Search
CPC .................. C07D 401/14; A61K 31/437
USPC .................................. 546/119; 514/303
See application file for complete search history.

(56) References Cited

U.S. PATENT DOCUMENTS 9,492,436 B2 * 11/2016 Himmelsbach ...... A61K 31/437
2013/0123237 A1 5/2013 Anand et al.

FOREIGN PATENT DOCUMENTS

WO 2014069426 A1 5/2014

OTHER PUBLICATIONS

Written Opinion of International Searching Authority for PCT/EP2016050557, Form PCT/ISA 237, dated Aug. 3, 2016.
International Search report, for PCT/EP2016/050558, Form PCT/ISA220, dated Aug. 3, 2016.
Abstract for WO2014069426, May 8, 2014.

* cited by examiner

*Primary Examiner* — Niloofar Rahmani
(74) *Attorney, Agent, or Firm* — Paula K. Wittmayer; David L. Kershner

(57) ABSTRACT

The present invention relates to compounds of general formula (I), wherein $R^1$, $R^2$, $R^3$, $A^1$, $A^2$, m and n are defined as in claim 1, which have valuable pharmacological properties, in particular bind to the AMP-activated protein kinase (AMPK) and modulate its activity. The compounds are suitable for treatment and prevention of diseases which can be influenced by this receptor, such as metabolic diseases, in particular diabetes type 2.

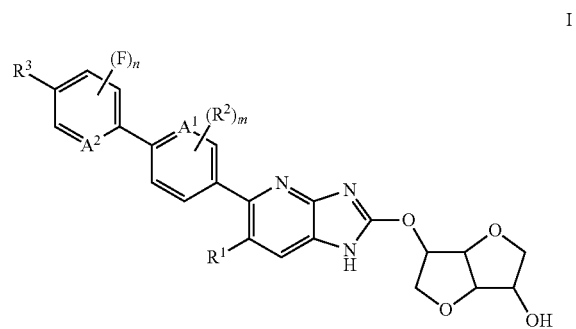

11 Claims, No Drawings

AZABENZIMIDAZOLE DERIVATIVES

FIELD OF THE INVENTION

The present invention relates to novel azabenzimidazole derivatives that are agonists of the AMP-activated protein kinase (AMPK), to processes for their preparation, to pharmaceutical compositions containing these compounds and to their medical use for the prophylaxis and/or treatment of diseases which can be influenced by the modulation of the function of AMPK. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease, dyslipidemia and kidney diseases such as diabetic nephropathy and chronic kidney disease.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, nephropathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

Sensing and regulating cellular the energy status in response to environmental and/or nutritional stress is highly important and AMP-activated protein kinase (AMPK) is a major contributor for this task (Hardie et al. (2001) Bioessays 23: 1112; Kemp et al. (2003) Biochem. Soc. Transactions 31: 162). Cellular energy depletion leads to the activation of AMP-activated protein kinase (AMPK) thereby inhibiting ATP consuming and upregulating ATP generating pathways. On a cellular level several substrates are regulated by AMP-activated protein kinase (AMPK) such as acetyl-CoA-carboxylase (ACC) and HMG-CoA-reductase (Carling et al. (1987) FEBS Letters 223: 217), hormone-sensitive lipase (Garton et al. (1989) Eur. J. Biochem. 179: 249), malonyl-CoA-decarboxylase (Saha et al. (2000) J. Biol. Chem. 275: 24279) and glycerol-3-phosphate acyltransferase (Muoio et al. (1999) Biochem. J. 338: 783).

AMP-activated protein kinase (AMPK) mediated phosphorylation of ACC leads to inhibition of ACC, which then results in a decrease of fatty acid synthesis while fatty acid oxidation is increased. AMP-activated protein kinase (AMPK) mediated phosphorylation and inhibition of HMG-CoA-reductase leads to a decrease in cholesterol synthesis. Triacylglycerol synthesis and fatty acid oxidation is regulated by AMP-activated protein kinase (AMPK) via glycerol-3-phosphate acyltransferase. In addition AMP-activated protein kinase (AMPK) stimulates glucose transport in skeletal muscle and regulates the expression of genes involved in fatty acid and glucose metabolism (Hardie et al. (2001) Bioessays 23: 1112; Kemp et al. (2003) Biochem. Soc. Transactions 31: 162). Glucose homeostasis is mediated in liver and muscle by AMP-activated protein kinase (AMPK), wherein activation of AMP-activated protein kinase (AMPK) leads to an increase in GLUT 4-dependent glucose uptake (Sakamoto et al. (2008) Am. J. Physiol. Endocrinol. Metab. 295: E29-E37; Karagounis et al. (2009) Int. J. Biochem. Cell Biol. 41: 2360-2363; Pehmøller et al. (2009) Am. J. Physiol. Endocrinol. Metab. 297: E665-E675).

Besides energy regulation on a cellular level AMP-activated protein kinase (AMPK) also regulates whole body energy metabolism. Independently of the cellular AMP level AMP-activated protein kinase (AMPK) can be activated by the adipocyte derived hormones leptin (Minokoski et al. (2002) Nature 415: 339) and adiponectin (Yamauchi et al. (2002) Nature Medicine 8: 1288).

From the points discussed above activation of AMP-activated protein kinase (AMPK) in vivo is expected to result in hepatic stimulation of fatty acid oxidation; inhibition of cholesterol synthesis, lipogenesis and triglyceride synthesis; stimulation of skeletal muscle fatty acid oxidation and glucose uptake; improved insulin action; increase in energy expenditure and hence a decrease in body weight.

OBJECT OF THE PRESENT INVENTION

The object of the present invention is to provide new compounds, hereinafter described as compounds of formula I, in particular new azabenzimidazole derivatives, which are active with regard to the AMP-activated protein kinase (AMPK), notably are agonists of the AMP-activated protein kinase (AMPK).

A further object of the present invention is to provide new compounds, in particular new azabenzimidazole derivatives, which have an activating effect on the AMP-activated protein kinase (AMPK) in vitro and/or in vivo and possess suitable pharmacological and pharmacokinetic properties to use them as medicaments.

A further object of the present invention is to provide effective agonists of AMP-activated protein kinase (AMPK), in particular for the treatment of metabolic disorders, for example diabetes, dyslipidemia and/or obesity.

A further object of the present invention is to provide methods for treating a disease or condition mediated by the activation the AMP-activated protein kinase (AMPK) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

AMP-activated protein kinase (AMPK) modulators are known in the art, for example, the compounds disclosed in WO 2012033149, WO 2012116145, WO 2013153479, WO 2014031515 and WO 2014069426. The azabenzimidazole derivatives of the present invention may provide several advantages, such as enhanced potency and/or efficacy, high metabolic and/or chemical stability, favorable pharmacokinetic profile, high selectivity and/or tolerability and in consequence low toxicity, reduced risk to cause adverse events or undesirable side effects, and enhanced solubility.

SUMMARY OF THE INVENTION

In a first aspect the invention relates to compounds of formula I containing three (consecutive) aromatic or heteroaromatic moieties

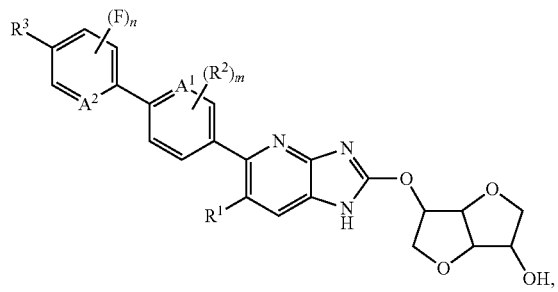

I wherein
$R^1$ is selected from the group $R^1$-G1 consisting of F and Cl,
$R^2$ is selected from the group $R^2$-G1 consisting of F and methoxy,
$R^3$ is selected from the group $R^3$-G1 consisting of

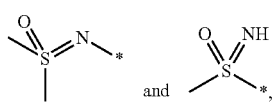

and $A^1$ is selected from the group $A^1$-G1 consisting of CH, $CR^2$ and N, $A^2$ is selected from the group $A^2$-G1 consisting of CH, CF and N,
m is selected from an integer consisting of 0, 1 and 2, and
n is selected from an integer consisting of 0, 1, and 2,
with the provisos, that at least one substituent attached to an aromatic or heteroaromatic moiety in formula I represents F or that $R^2$ represents methoxy,
the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, $R^1$-G1 defines genus 1 of the substituent $R^1$.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the AMP-activated protein kinase (AMPK) in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided a method for treating a cardiovascular disease or disorder, such as myocardial infarction, stroke, heart failure, coronary artery disease, hypertension, in a patient in need thereof characterized in that a therapeutically effective amount of a compound of general formula I or a pharmaceutically acceptable salt thereof is administered to the patient.

According to another aspect of the invention, there is provided a method for treating a kidney disease or disorder, such as diabetic nephropathy, chronic kidney disease, acute kidney injury and/or polycystic kidney disease, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the AMP-activated protein kinase (AMPK) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the AMP-activated protein kinase (AMPK).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$, $R^3$, $A^1$ and $A^2$ are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:

$R^1$-G1:
The group $R^1$ is preferably selected from the group $R^1$-G1 as defined hereinbefore.

$R^1$-G2a:
In another embodiment the group $R^1$ is selected from the group $R^1$-G2a consisting of F.

$R^1$-G2b:
In another embodiment the group $R^1$ is selected from the group $R^1$-G2b consisting of Cl.

$R^2$:

$R^2$-G1:
The group $R^2$ is preferably selected from the group $R^2$-G1 as defined hereinbefore.

$R^2$-G2a:
In another embodiment the group $R^2$ is selected from the group $R^2$-G2a consisting of F.

$R^2$-G2b:
In another embodiment the group $R^2$ is selected from the group $R^2$-G2b consisting of methoxy.

$R^3$:

$R^3$-G1:
The group $R^3$ is preferably selected from the group $R^3$-G1 as defined hereinbefore.

$R^3$-G2a:
In another embodiment the group $R^3$ is selected from the group $R^3$-G2a consisting of

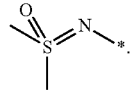

$R^3$-G2b:
In another embodiment the group $R^3$ is selected from the group $R^3$-G2b consisting of

$A^1$:

$A^1$-G1:
The group $A^1$ is preferably selected from the group $A^1$-G1 as defined hereinbefore.

$A^1$-G2a:
In another embodiment the group $A^1$ is selected from the group $A^1$-G2a consisting of CH and $CR^2$.

$A^1$-G2b:
In another embodiment the group $A^1$ is selected from the group $A^1$-G2b consisting of N.

$A^2$:

$A^2$-G1:
The group $A^1$ is preferably selected from the group $A^2$-G1 as defined hereinbefore.

$A^2$-G2a:
In another embodiment the group $A^2$ is selected from the group $A^2$-G2a consisting of CH and CF.

$A^2$-G2b:
In another embodiment the group $A^2$ is selected from the group $A^2$-G2b consisting of N.

PREFERRED EMBODIMENTS

In a preferred embodiment the invention relates to compounds of formula II containing a biphenylyl-azabenzimidazole moiety

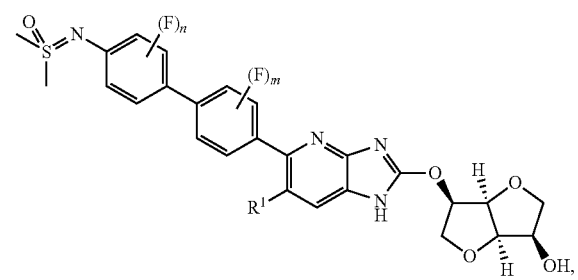

wherein
$R^1$ is selected from the group $R^1$-G1 consisting of F and Cl,
m is selected from an integer consisting of 0, 1 and 2, and
n is selected from an integer consisting of 0, 1, and 2,
with the proviso, that at least one substituent attached to the biphenylyl-azabenzimidazole moiety represents F,
the isoforms, tautomers, stereoisomers, metabolites, prodrugs, solvates, hydrates, and the salts thereof, particularly the physiologically acceptable salts thereof with inorganic or organic acids or bases, or the combinations thereof.

In another preferred embodiment the invention relates to compounds of formula III containing a biphenylyl-azabenzimidazole moiety

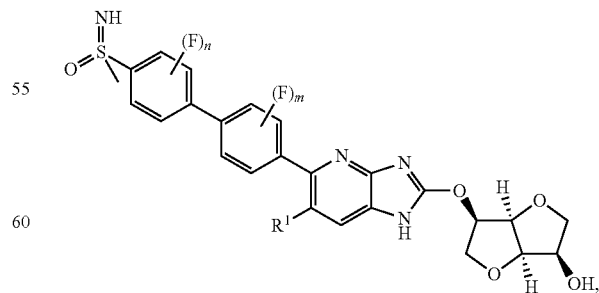

wherein
$R^1$ is selected from the group $R^1$-G1 consisting of F and Cl,
m is selected from an integer consisting of 0, 1 and 2, and
n is selected from an integer consisting of 0, 1, and 2, with the proviso, that at least one substituent attached to the biphenylyl-azabenzimidazole moiety represents F, the isoforms, tautomers, stereoisomers, metabolites, prodrugs, solvates, hydrates, and the salts thereof, particularly the physiologically acceptable salts thereof with inorganic or organic acids or bases, or the combinations thereof.

In another preferred embodiment the invention relates to compounds of formula IV

IV

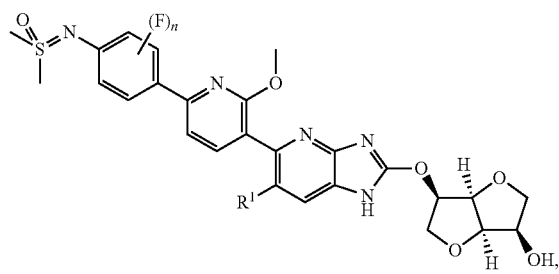

wherein
$R^1$ is selected from the group $R^1$-G1 consisting of F and Cl, and
n is selected from an integer consisting of 0, 1, and 2, the isoforms, tautomers, stereoisomers, metabolites, prodrugs, solvates, hydrates, and the salts thereof, particularly the physiologically acceptable salts thereof with inorganic or organic acids or bases, or the combinations thereof.

In another preferred embodiment the invention relates to compounds of formula V

V

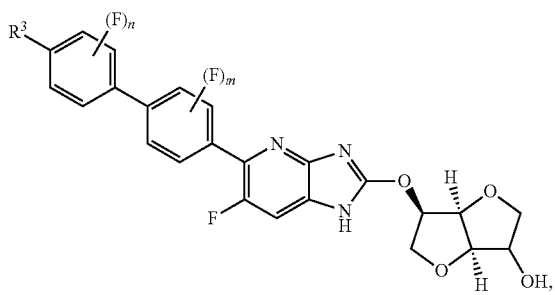

wherein
$R^3$ is selected from the group $R^3$-G1 consisting of

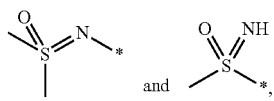
and m is selected from an integer consisting of 0, 1 and 2, and
n is selected from an integer consisting of 0, 1, and 2, the isoforms, tautomers, stereoisomers, metabolites, prodrugs, solvates, hydrates, and the salts thereof, particularly the physiologically acceptable salts thereof with inorganic or organic acids or bases, or the combinations thereof.

In another preferred embodiment the invention relates to compounds of formula VI

VI

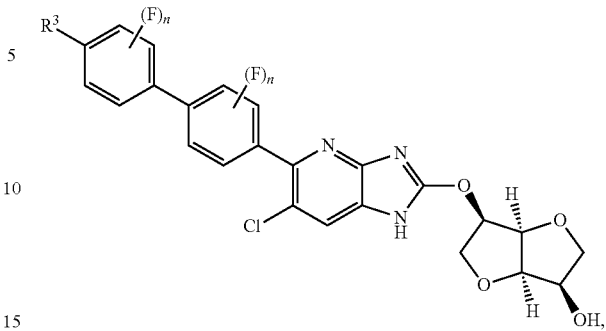

wherein
$R^3$ is selected from the group $R^3$-G1 consisting of

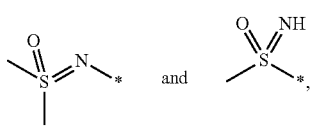

m is selected from an integer consisting of 0, 1 and 2, and
n is selected from an integer consisting of 0, 1, and 2,
with the proviso, that at least one of m and n denotes 1 or 2, the isoforms, tautomers, stereoisomers, metabolites, prodrugs, solvates, hydrates, and the salts thereof, particularly the physiologically acceptable salts thereof with inorganic or organic acids or bases, or the combinations thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled person on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled person.

The compounds of the invention I are preferably accessed from a precursor 1a or 1b which bears a protecting group at the imidazopyridine-nitrogen in position 3 or 1 (Scheme 1); $A^1$, $A^2$, $R^1$, $R^2$, $R^3$ and $R^{3'}$ have the meaning as defined hereinbefore and hereinafter. For the sake of convenience only the $N^3$ protected species (1a in Scheme 1) will be shown hereinafter, although by and large all transformations described below are also applicable to the $N^1$ protected series (1b in Scheme 1).

butyloxycarbonyl group can be cleaved under acidic conditions such as HCl, $H_2SO_4$, $CF_3CO_2H$, $MeSO_3H$, $KHSO_4$, $HCO_2H$, $BF_3 \times OEt_2$ in a solvent such as dichloromethane,

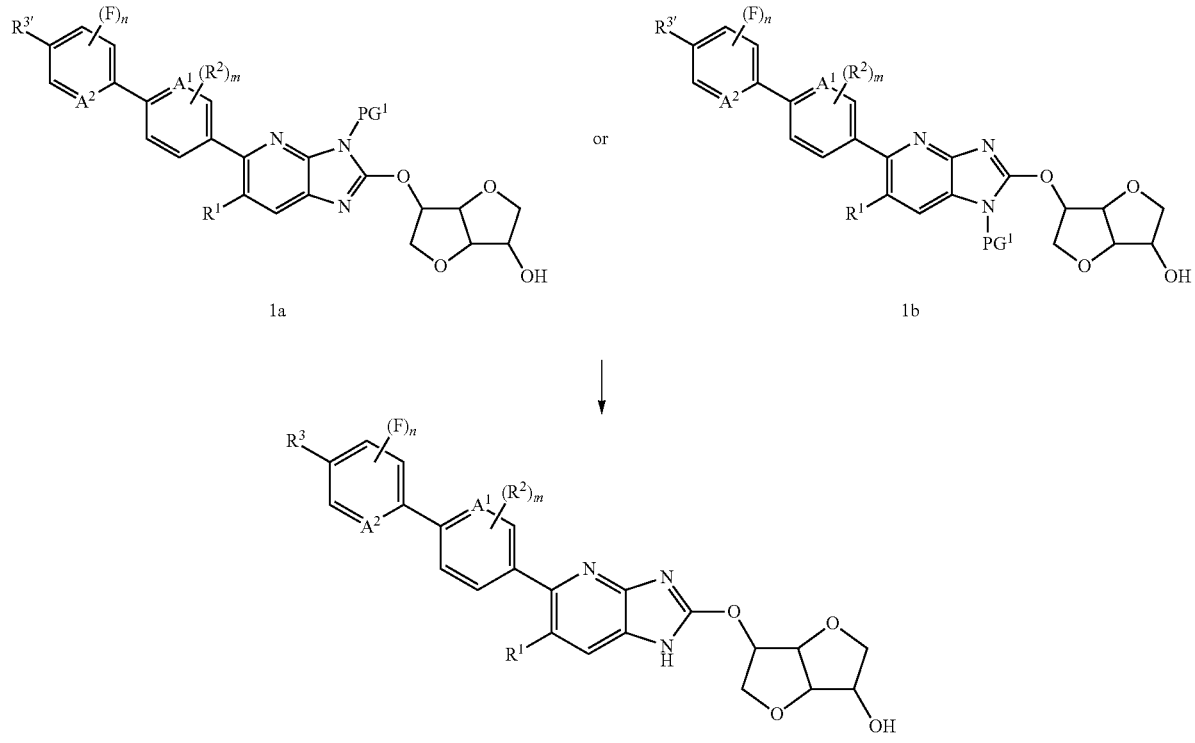

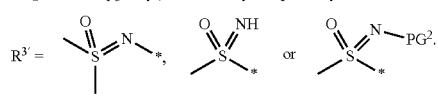

The benzyl protecting group is cleaved advantageously using hydrogen in the presence of a transition metal, preferably palladium on carbon in a solvent such as methanol, ethanol, tetrahydrofuran, 1,4-dioxane. Benzyl groups bearing electron donating groups on the phenyl ring, such as methoxy, may also be removed under acidic conditions such as $H_2SO_4$ or $CF_3CO_2H$, $MeSO_3H$. Amino-acetal derivatives can be cleaved under acidic conditions such as HCl, $H_2SO_4$, $CF_3CO_2H$, $MeSO_3H$, $KHSO_4$, $HCO_2H$, $BF_3 \times OEt_2$ in a solvent such as dichloromethane, water, tetrahydrofuran, 1,4-dioxane or mixtures thereof at −10 to 100° C. In addition to cleavage under acidic conditions, amino-acetal derivatives bearing a $Si(CH_3)_3$ group can also be cleaved in the presence of tetrabutylammonium fluoride.

The N atom of the sulfoximine moiety $R^3$ might be protected with a suitable protecting group $PG^2$, e.g. a benzyloxy-carbonyl, tert-butoxycarbonyl, acetyl, or 2,2,2-trifluoroacetyl group. The protecting group $PG^2$ is either removed together with $PG^1$ in one reaction step or in an additional deprotection step, depending on the nature of $PG^1$ and $PG^2$. The benzyloxy-carbonyl group is cleaved advantageously using hydrogen in the presence of a transition metal, preferably palladium on carbon in a solvent such as methanol, ethanol, tetrahydrofuran, 1,4-dioxane. The tert.- water, tetrahydrofuran, 1,4-dioxane or mixtures thereof at −10 to 100° C. The 2,2,2-trifluoroacetyl group can be cleaved under basic conditions such as $K_2CO_3$, NaOH, KOH, NaOMe, NaOEt, NaOtBu in a solvent such as water, methanol, tetrahydrofuran, 1,4-dioxane or mixtures thereof at −10 to 50° C.

Compounds 1 can be prepared from imidazopyridine derivatives 2 and boronic acid derivatives 3 (Scheme 2); $A^1$, $A^2$, $R^1$, $R^2$, $R^{3'}$ have the meaning defined hereinbefore and hereinafter.

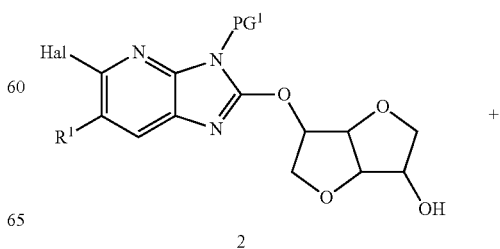

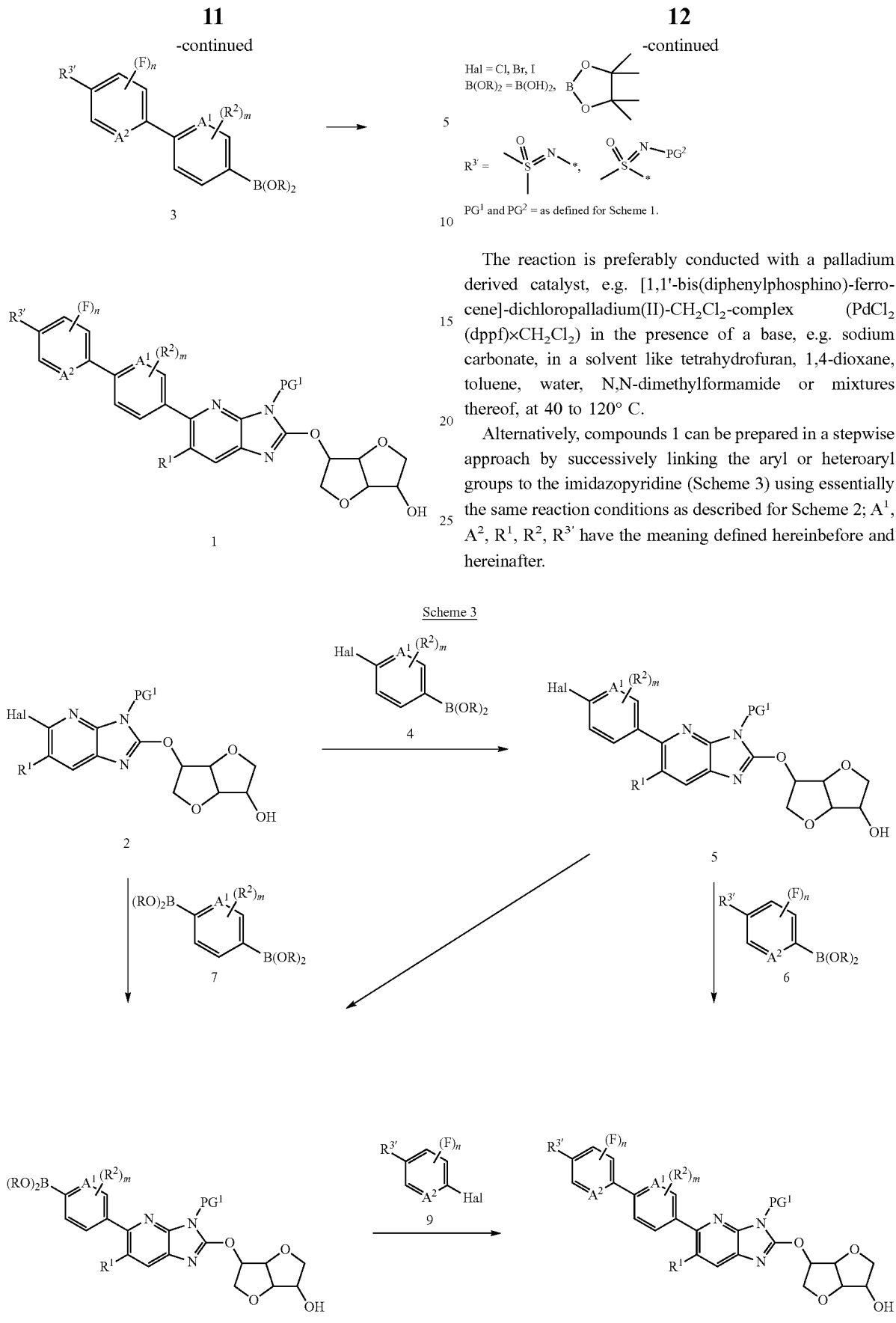

The reaction is preferably conducted with a palladium derived catalyst, e.g. [1,1'-bis(diphenylphosphino)-ferrocene]-dichloropalladium(II)-CH$_2$Cl$_2$-complex (PdCl$_2$(dppf)×CH$_2$Cl$_2$) in the presence of a base, e.g. sodium carbonate, in a solvent like tetrahydrofuran, 1,4-dioxane, toluene, water, N,N-dimethylformamide or mixtures thereof, at 40 to 120° C.

Alternatively, compounds 1 can be prepared in a stepwise approach by successively linking the aryl or heteroaryl groups to the imidazopyridine (Scheme 3) using essentially the same reaction conditions as described for Scheme 2; $A^1$, $A^2$, $R^1$, $R^2$, $R^{3'}$ have the meaning defined hereinbefore and hereinafter.

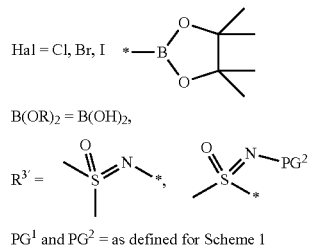

Compounds 1' bearing a sulfoximine linked via the nitrogen to an aryl or heteroaryl group can be prepared from halogen compounds 10 via direct coupling of the sulfoximine (Scheme 4); $A^1$, $A^2$, $R^1$, $R^2$ have the meaning defined hereinbefore and hereinafter.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again

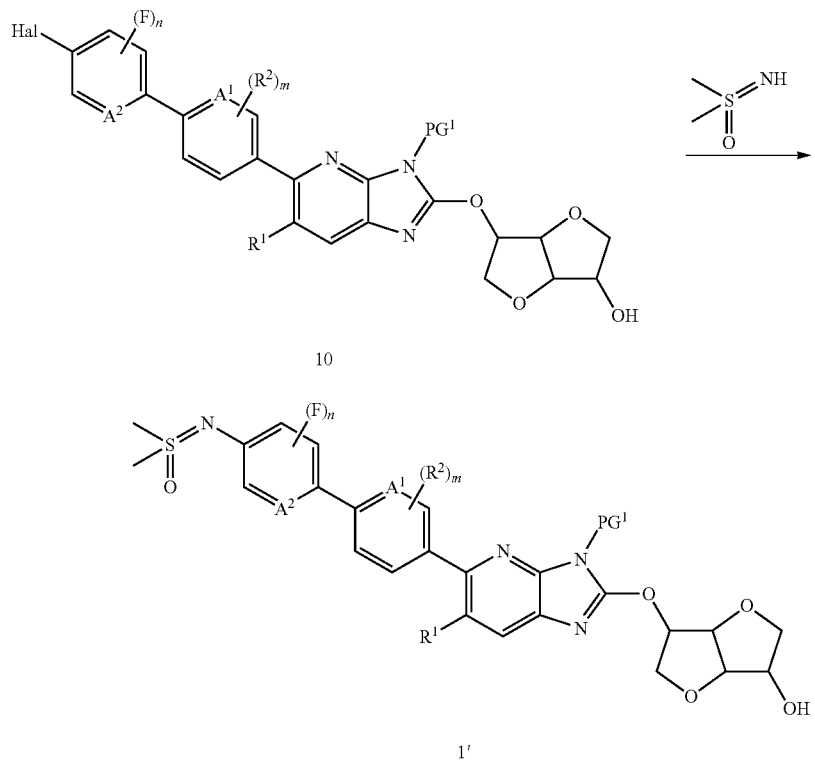

The coupling reaction is preferably conducted with a palladium derived catalyst and a suitable ligand, e.g. tris(dibenzylideneacetone)dipalladium(0) and 4,5-bis(diphenylphosphino)-9,9-dimethylxanthene (Xantphos) or 2-(di-t-butylphosphino)bipheny, palladium(II) acetate and 2-dicyclohexylphosphino-2',6'-di-isopropoxy-1,1'-biphenyl (RuPhos), or palladium(II) acetate and racemic 2,2'-bis-(diphenylphosphino)-1,1'-binaphthyl in the presence of a base, e.g. cesium carbonate or sodium tert-butoxide in a suitable solvent such as 1,4-dioxane or toluene at 40 to 120° C.

after the reaction. Suitable protecting groups for the respective functionalities and their removal are well known to the one skilled in the art and are described in the literature of organic synthesis.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physicochemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physicochemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the AMP-activated protein kinase (AMPK) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

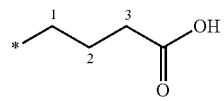

wherein the carboxy group is attached to the third carbon atom of the propyl group. The terms "1-methylpropyl-", "2,2-dimethylpropyl-" or "cyclopropylmethyl-" group represent the following groups:

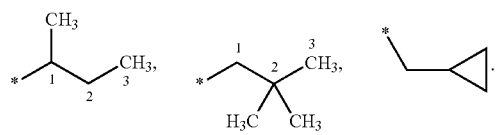

The asterisk may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

Pharmacological Activity

The activity of the compounds of the invention may be demonstrated using the following in vitro AMPK activation assays:

AMPK α1β1γ1:

Recombinant human AMPK (containing subunits alpha1, beta1 and gamma1) was obtained from a baculovirus expression system. The 3 subunits were expressed together, affinity-purified via a GST-tag fused to the alpha 1 subunit and deep-frozen in storage buffer (50 mM Tris-HCl pH 8, 300 mM NaCl, 1 mM TCEP and 10% glycerol) at −80° C. until use. The activity of the AMPK protein was determined using the ADP Glo® Luminescence Kinase test (Promega; V9103X). In this homogeneous test the amount of ADP formed by the kinase reaction is quantified by a luciferin-luciferase reaction using luminescence as read-out. The luminescence signal obtained correlates with the amount of ADP resulting from the kinase reaction and thus correlates with the activity of the protein kinase.

Method:

The test compounds were dissolved in 100% DMSO at a concentration of 10 mM and in a first step diluted in DMSO to a concentration of 5 mM, followed by serial dilution steps in 100% DMSO. Dilution factor and number of dilution steps may vary. Typically 8 different concentrations by 1:5 dilutions were prepared, further dilutions of the substances were carried out with test buffer (20 mM Hepes (pH 7.0), 15 mM $MgCl_2$, 0.025% BSA, 0.01% Brij 35) until a concentration was reached which was 5 times above the final test concentration. 2 μl aliquots of these dilutions were transferred into a 384-well Optiplate (Perkin Elmer, #6007290). Typically the start concentration for serial dilutions in the assay is 10 μM. Typically AMPK was diluted to 25 μg/ml in the test buffer and 4 μl of this dilution were used in the kinase test (final concentration of AMPK is 10 μg/ml in a total volume of 10 μl for the kinase reaction). Kinase concentrations may vary depending on activity of the preparation batches. After 10 minutes incubation at room temperature 4 μl of a mix containing 2.5 μM substrate (H-His-Met-Arg-Ser-Ala-Met-Ser-Gly-Leu-His-Leu-Val-Lys-Arg-Arg-OH Trifluoroacetate salt/HMRSAMSGLHLVKRR from Bachem, Cat. No. H5938) and 75 μM ATP in test buffer were added to each well and the incubation was continued for 60 minutes at room temperature.

Positive controls are the reaction mixtures that contain no test substance; negative controls (blanks) are reaction mixtures that contain no AMPK enzyme.

After 60 minutes, 10 μl ADP-Glo® solution (ADP-Glo Reagent #V912B Promega) (heated to room temperature) were added to each well and incubation was continued for 40 minutes. Then 20 μl Kinase detection mix (Detection Buffer #V913B Promega; Kinase Detection Substrate #V914B Promega) were added and incubated for additional 40 minutes at room temperature.

All incubations were done in sealed plates in the dark.

The plates were read with an Envision Luminescence Reader (Perkin-Elmer).

Data Evaluation and Calculation:

The output file of the reader is a csv file that contains the well number and measured RLU. For data evaluation and calculation, the measurement of the negative control was set as 0% control and the measurement of the positive control was set as 100% control. Based on these values the % value for the measurement of each substance concentration was calculated using Assay Explorer software (Accelrys). Activating compounds achieve % of control values above 100%. The $IC_{50}$ values were calculated from the % control values using Assay Explorer software. Calculation: $[y=(a-d)/(1+(x/c)^b)+d]$, a=low value, d=high value; x=conc M; c=$IC_{50}$ M; b=hill; y=% ctrl. The maximal achievable activation of a compound in the tested concentration range is reported as percent of control max (PoCmax).

The compounds according to the invention typically have $EC_{50}$ values in the range from about 0.1 nM to about 10 μM, preferably less than 1 μM, more preferably less than 300 nM.

$EC_{50}$ and PoCmax values for compounds according to the invention are shown in the following table. The number of the compound corresponds to the number of the Example in the experimental section.

| Example | AMPK α1β1γ1 $EC_{50}$ [nM] | AMPK α1β1γ1 PoCmax [%] |
| --- | --- | --- |
| 1 | 284 | 540 |
| 2 | 115 | 496 |
| 3 | 302 | 480 |
| 4 | 3564 | 421 |
| 5 | 60 | 538 |
| 6 | 450 | 490 |
| 7 | 125 | 640 |
| 8 | 255 | 659 |
| 9 | 282 | 700 |
| 10 | 193 | 479 |
| 11 | 1200 | 423 |
| 12 | 109 | 608 |
| 13 | 71 | 523 |
| 14 | 68 | 484 |
| 15 | 344 | 426 |
| 16 | 74 | 475 |
| 17 | 84 | 475 |

In view of their ability to modulate the activity of the AMP-activated protein kinase (AMPK), in particular an agonistic activity, the compounds of general formula I according to the invention, including the corresponding salts thereof, are theoretically suitable for the treatment of all those diseases or conditions which may be affected or which are mediated by the activation of the AMP-activated protein kinase (AMPK).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the AMP-activated protein kinase (AMPK) in a patient, preferably in a human.

In yet another aspect the present invention relates to a method for treating a disease or condition mediated by the activation of the AMP-activated protein kinase (AMPK) in a mammal that includes the step of administering to a patient, preferably a human, in need of such treatment a therapeutically effective amount of a compound or a pharmaceutical composition of the present invention.

Diseases and conditions mediated by agonists of the AMP-activated protein kinase (AMPK) embrace metabolic diseases or conditions. According to one aspect the compounds and pharmaceutical compositions of the present invention are particularly suitable for treating diabetes mellitus, in particular Type 2 diabetes, Type diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

- for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);
- for improving glycaemic control and/or reducing fasting plasma glucose, postprandial plasma glucose and/or the glycosylated haemoglobin HbA1c;
- for preventing, delaying, slowing or reversing the progression of disrupted glucose tolerance, insulin resistance and/or metabolic syndrome to type 2 diabetes;
- for preventing, delaying, slowing the progression of or treating a condition or a disease selected from among the complications of diabetes, such as for example retinopathy, nephropathy or neuropathies, diabetic foot, ulcers or macroangiopathies;
- for reducing weight or preventing weight gain or assisting weight loss;
- for preventing or treating the degradation of pancreatic beta cells and/or improving and/or restoring the functionality of pancreatic beta cells and/or restoring the functionality of pancreatic insulin secretion;
- for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 20 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PCSK9 inhibitors, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the AMP-activated protein kinase (AMPK), in particular diseases or conditions as described hereinbefore and hereinafter.

In yet another aspect the present invention relates a method for treating a disease or condition mediated by the activation of the AMP-activated protein kinase (AMPK) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm.

The terms "ambient temperature" and "room temperature" are used interchangeably and designate a temperature of about 20° C.

Analytical HPLC parameters employed for characterization of products (TFA denotes trifluoroacetic acid and FA denotes formic acid):

| Method: 1 Device: Agilent 1200 with DA and MS detector Column: XBridge C18, 3.0 × 30 mm, 2.5 μm Column Supplier: Waters | | | | |
|---|---|---|---|---|
| Gradient/ Solvent Time [min] | % Solvent [H$_2$O, 0.1% TFA] | % Solvent [Acetonitrile] | Flow [mL/min] | Temperature [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 2
Device: Agilent 1200 with DA and MS detector
Column: Sunfire C18, 3.0 × 30 mm, 2.5 μm
Column Supplier: Waters

| Gradient/ Solvent Time [min] | % Solvent [H₂O, 0.1% TFA] | % Solvent [CH₃CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 3
Device: Agilent 1200 with DA and MS detector
Column: Sunfire C18, 3.0 × 30 mm, 2.5 μm
Column Supplier: Waters

| Gradient/ Solvent Time [min] | % Solvent [H₂O, 0.1% TFA] | % Solvent [Acetonitrile] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 4
Device: Agilent 1100 with DA and MS detector
Column: Sunfire C18, 4.6 × 30 mm, 3.5 μm
Column Supplier: Waters

| Gradient/ Solvent Time [min] | % Solvent [H₂O, 0.1% TFA] | % Solvent [Acetonitrile] | Flow [mL/min] | Temperature [° C.] |
|---|---|---|---|---|
| 0.00 | 95 | 5 | 4.0 | 60 |
| 0.15 | 95 | 5 | 4.0 | 60 |
| 1.70 | 0 | 100 | 4.0 | 60 |
| 2.25 | 0 | 100 | 4.0 | 60 |

Method: 5
Device: Agilent 1200 with DA and MS detector
Column: XBridge C18, 3 × 30 mm, 2.5 μm
Column Supplier: Waters

| Gradient/ Solvent Time [min] | % Solvent [H₂O, 0.1% TFA] | % Solvent [CH₃CN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

The Examples that follow are intended to illustrate the present invention without restricting it:

Intermediate 1

(3R,3aR,6R,6aR)-6-(6-Chloro-5-iodo-3-(2-trimethylsilanyl-ethoxymethyl)-3H-imidazo[4,5-b]pyridin-2-yloxy)hexahydrofuro[3,2-b]furan-3-ol

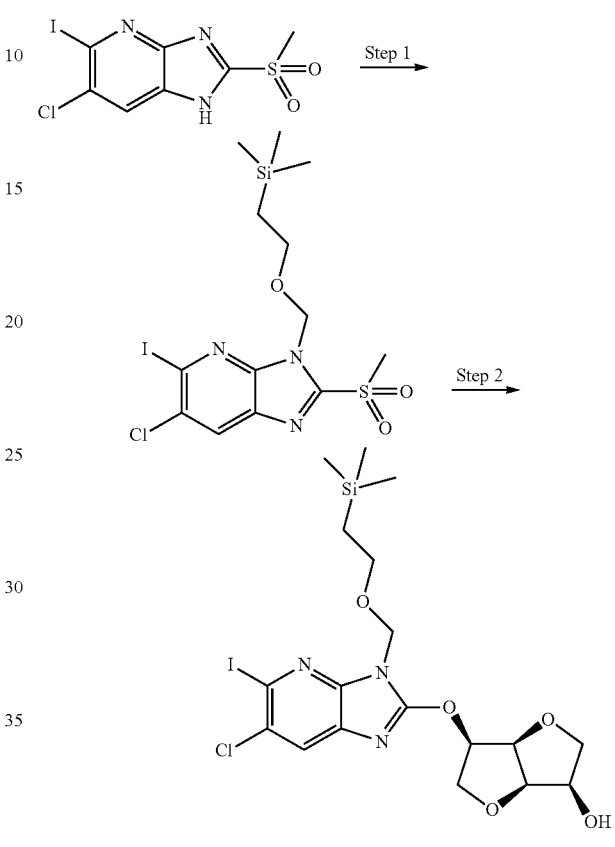

Step 1: 6-Chloro-5-iodo-2-(methylsulfonyl)-3-(2-trimethylsilanyl-ethoxymethyl)-3H-imidazo[4,5-b] pyridine 6-Chloro-5-iodo-2-(methylsulfonyl)-1H-imidazo[4,5-b] pyridine (for preparation see WO 2012116145; 1.5 g) and triethylamine (875 μL) are dissolved in tetrahydrofurane (12 mL), cooled to 0° C. and treated with (2-(chloromethoxy) ethyl)trimethylsilane (SEM-Cl; 890 μL). The mixture is stirred for 30 minutes while warming to room temperature. Then the mixture is partitioned between saturated aqueous NH₄Cl and ethylacetate. The organic phase is washed with water and brine. After drying (MgSO₄) the solvents are evaporated in vacuo to give the title compound. LC (method 1): $t_R$=1.22 min; Mass spectrum (ESI⁺): m/z=488 [M+H]⁺.

Step 2: (3R,3aR,6R,6aR)-6-(6-Chloro-5-iodo-3-(2-trimethylsilanyl-ethoxymethyl)-3H-imidazo[4,5-b]pyridin-2-yloxy)hexahydrofuro[3,2-b]furan-3-ol (3R,3aR,6R,6aR)-Hexahydrofuro[3,2-b]furan-3,6-diol (1.84 g) is dissolved in N,N-dimethylformamide (10 mL) and treated with 1,8-diazabicyclo[5.4.0]undec-7-ene (DBU; 1.9 mL). A solution of 6-chloro-5-iodo-2-(methylsulfonyl)-3-(2-trimethylsilanyl-ethoxymethyl)-3H-imidazo[4,5-b] pyridine (2.05 g) in N,N-dimethylformamide (20 mL) is added drop wise and the mixture is stirred for 2 hours at room temperature. The mixture is partitioned between water and ethylacetate and the organic phase is washed with brine and dried (MgSO$_4$). The solvents are evaporated in vacuo and the residue is chromatographed on silica gel (cyclohexane/ethyl acetate 80:20→0:100) to give the title compound. LC (method 1): $t_R$=1.17 min; Mass spectrum (ESI$^+$): m/z=554 [M+H]$^+$.

Intermediate 2

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2-fluorophenyl}imino)dimethyl-λ$^6$-sulfanone

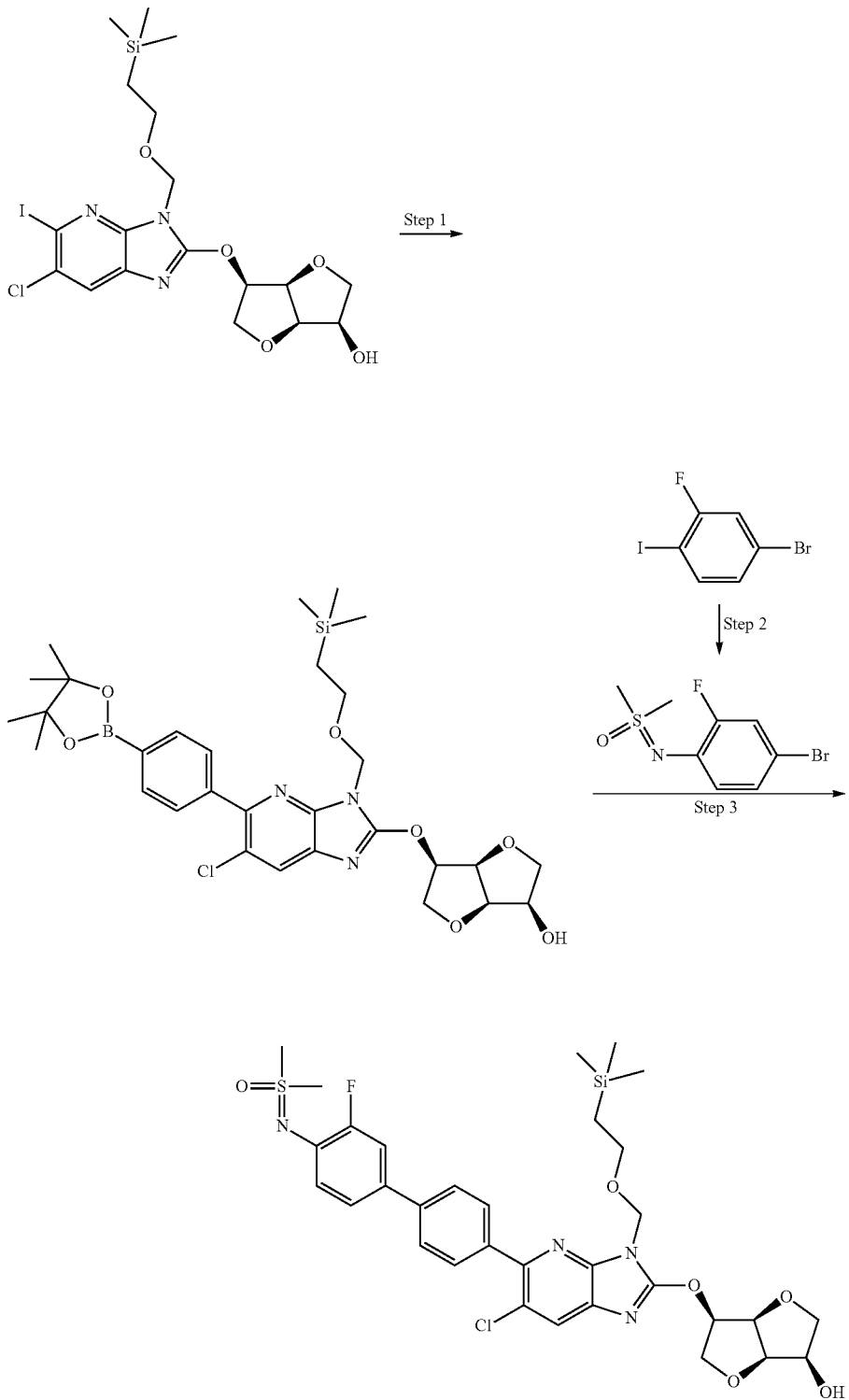

Step 1: (3R,3aR,6R,6aR)-6-(6-Chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol A mixture of (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol (2.00 g), 1,4-benzenediboronic acid dipinacol ester (2.38 g), saturated aqueous solution of $Na_2CO_3$ (5.42 mL), and 1,4-dioxane (15.00 mL) is purged with argon for 5 min. [1,1'-Bis-(diphenylphosphino)-ferrrocen]-dichlorpalladium(II)-$CH_2Cl_2$-complex (206 mg) is added and the mixture is stirred overnight at 70° C. The reaction mixture is washed with water and brine, dried over $MgSO_4$, and concentrated in vacuo. The residue is chromatographed on silica gel (dichloromethane/methanol 99:1→97:3) to give the title compound. LC (method 1): $t_R$=1.28 min; Mass spectrum (ESI$^+$): m/z=630 [M+H]$^+$.

Step 2: [(4-Bromo-2-fluorophenyl)imino]dimethyl-$\lambda^6$-sulfanone

S,S-Dimethylsulfoximine (186 mg) and $Cs_2CO_3$ (758 mg) are added to a solution of 4-bromo-2-fluoro-1-iodo-benzene (500 mg) in 1,4-dioxane (15 mL) and the mixture is purged with argon for several minutes. 4,5-Bis(diphenylphosphino)-9,9-dimethylxanthene (Xantphos, 72 mg) and tris(dibenzylideneacetone)dipalladium(0) (46 mg) are added and the reaction mixture is stirred for 3 h at 100° C. After cooling to room temperature methanol is added and the mixture is filtered through Celite. The filtrate is concentrated in vacuo and the residue is chromatographed on silica gel (cyclohexane/ethyl acetate 70:30→50:50).

LC (method 2): $t_R$=0.98 min; Mass spectrum (ESI$^+$): m/z=266 [M+H]$^+$.

Step 3: ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2-fluorophenyl}imino)dimethyl-$\lambda^6$-sulfanone A saturated aqueous solution of $Na_2CO_3$ (875 μL) is added to a mixture of (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol (440 mg) and [(4-bromo-2-fluorophenyl)imino]dimethyl-$\lambda^6$-sulfanone (230 mg) in 1,4-dioxane (8 mL) and the resulting mixture is purged with argon for 5 min. Bis-(diphenylphosphino)-ferrrocen]-dichlorpalladium(II)-$CH_2Cl_2$-complex (58 mg) is added and the reaction mixture is stirred overnight at 80° C. After cooling to room temperature the mixture is diluted with water and dichloromethane.

The organic phase is separated, dried over $MgSO_4$ and concentrated in vacuo. The residue is dissolved in a mixture of tetrahydrofuran/methanol/N,N-dimethylformamide (2:1:1) and filtered. The filtrate is directly submitted to HPLC on reversed phase to give the title compound. LC (method 2): $t_R$=1.13 min; Mass spectrum (ESI$^+$): m/z=689 [M+H]$^+$ Intermediate 3

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3,5-difluorophenyl}imino)dimethyl-$\lambda^6$-sulfanone

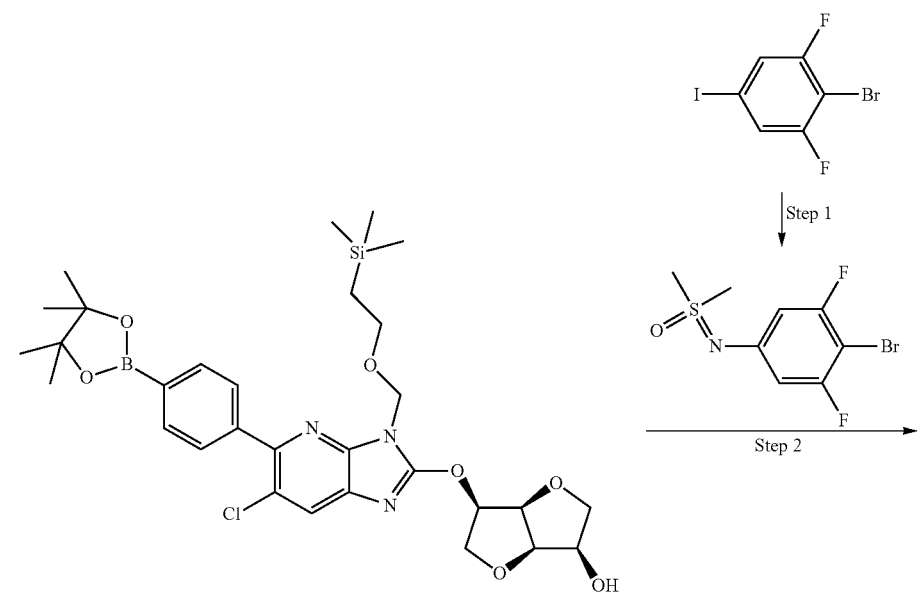

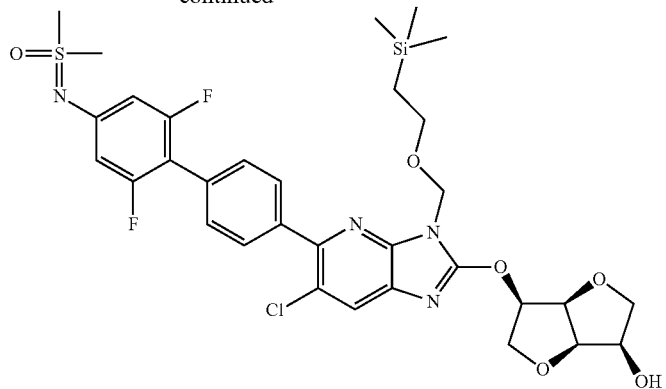

Step 1: [(4-Bromo-3,5-difluorophenyl)imino]dimethyl-λ⁶-sulfanone

The title compound is prepared from 2-bromo-1,3-difluoro-5-iodo-benzene and S,S-dimethylsulfoximine following a procedure analogous to that described for Intermediate 2 (Step 2). LC (method 2): $t_R$=0.95 min; Mass spectrum (ESI⁺): m/z=284 [M+H]⁺.

Step 2: ({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3,5-difluorophenyl}imino)dimethyl-λ⁶-sulfanone The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and [(4-bromo-3,5-difluorophenyl)imino]dimethyl-λ⁶-sulfanone following a procedure analogous to that described for Intermediate 2 (Step 3). LC (method 2): $t_R$=1.15 min; Mass spectrum (ESI⁺): m/z=707 [M+H]⁺.

Intermediate 4

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,5-difluorophenyl}imino)dimethyl-λ⁶-sulfanone

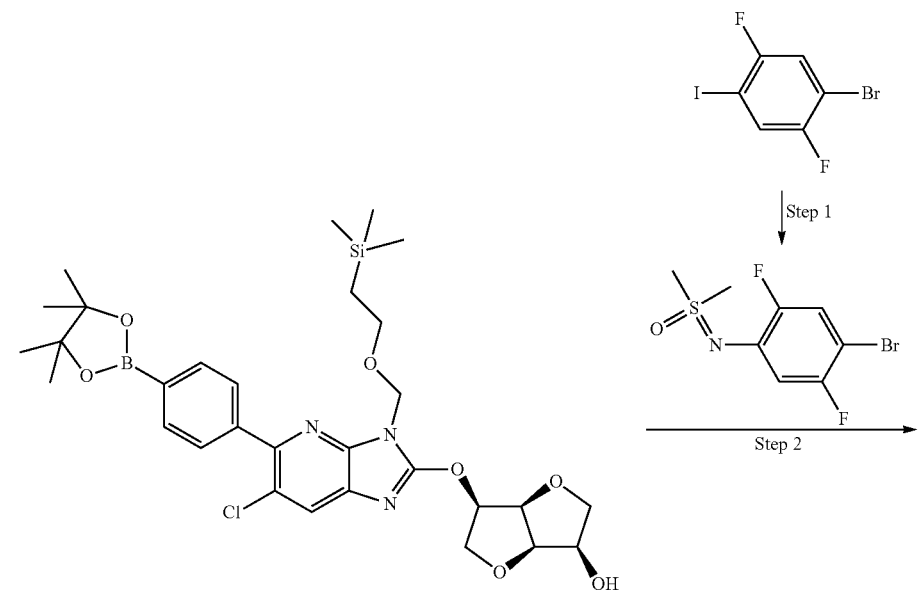

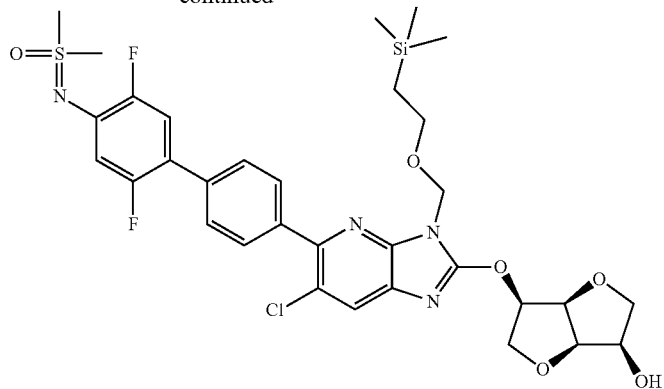

Step 1: [(4-Bromo-2,5-difluorophenyl)imino]dimethyl-λ⁶-sulfanone

The title compound is prepared from 1-bromo-2,5-difluoro-4-iodo-benzene and S,S-dimethylsulfoximine following a procedure analogous to that described for Intermediate 2 (Step 2). LC (method 2): $t_R$=0.93 min; Mass spectrum (ESI⁺): m/z=284 [M+H]⁺.

Step 2: ({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,5-difluorophenyl}imino)dimethyl-λ⁶-sulfanone The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and [(4-bromo-2,5-difluorophenyl)imino]dimethyl-λ⁶-sulfanone following a procedure analogous to that described for Intermediate 2 (Step 3). LC (method 2): $t_R$=1.15 min; Mass spectrum (ESI⁺): m/z=707 [M+H]⁺.

Intermediate 5

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,6-difluorophenyl}imino)dimethyl-λ⁶-sulfanone

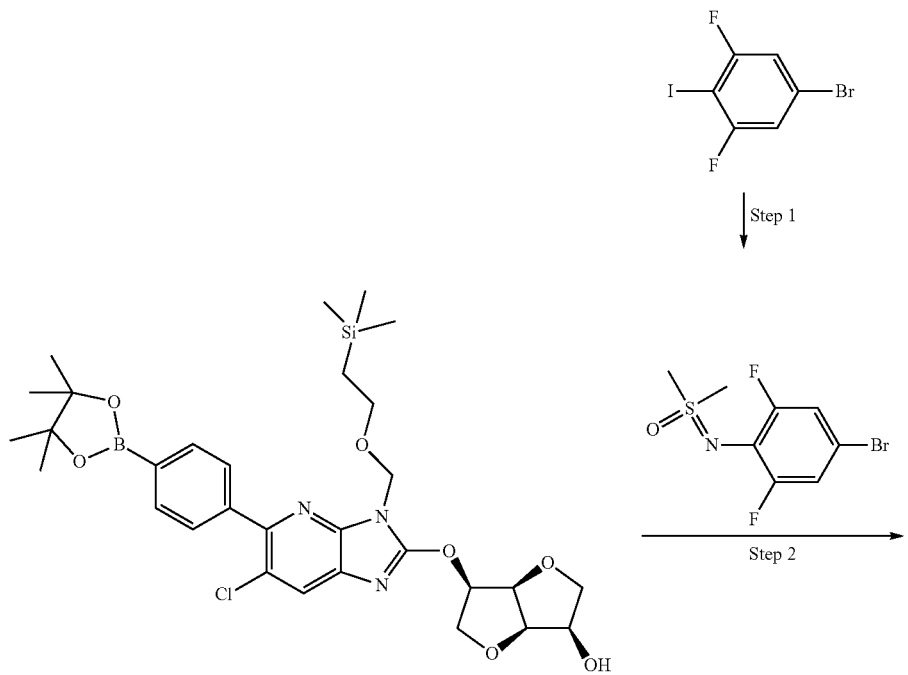

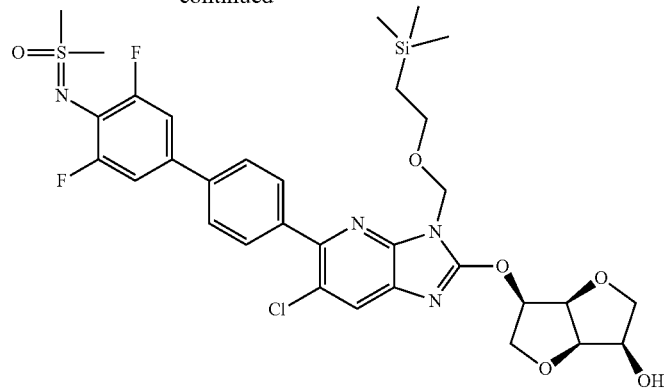

Step 1: [(4-Bromo-2,6-difluorophenyl)imino]dimethyl-λ⁶-sulfanone

The title compound is prepared from 5-bromo-1,3-difluoro-2-iodobenzene and S,S-dimethylsulfoximine following a procedure analogous to that described for Intermediate 2 (Step 2). LC (method 2): $t_R$=0.90 min; Mass spectrum (ESI⁺): m/z=284 [M+H]⁺.

Step 2: ({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,6-difluorophenyl}imino)dimethyl-λ⁶-sulfanone The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and [(4-bromo-2,6-difluorophenyl)imino]dimethyl-λ⁶-sulfanone following a procedure analogous to that described for Intermediate 2 (Step 3). LC (method 2): $t_R$=1.14 min; Mass spectrum (ESI⁺): m/z=707 [M+H]⁺.

Intermediate 6

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3-fluorophenyl}imino)dimethyl-λ⁶-sulfanone

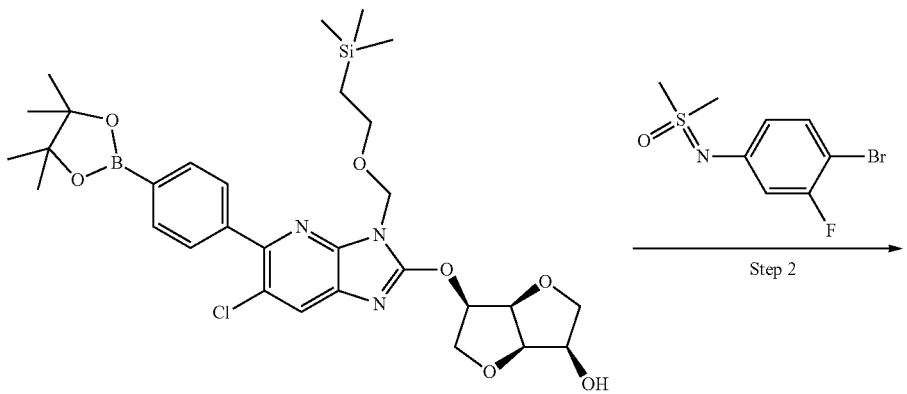

-continued

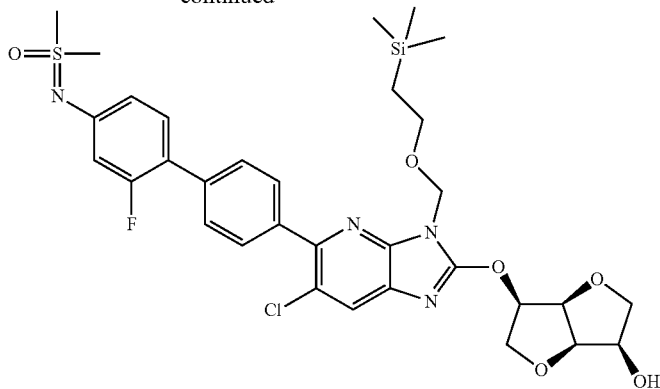

Step 1: [(4-Bromo-3-fluorophenyl)imino]dimethyl-λ⁶-sulfanone

The title compound is prepared from 1-bromo-2-fluoro-4-iodo-benzene and S,S-dimethylsulfoximine following a procedure analogous to that described for Intermediate 2 (Step 2). LC (method 2): $t_R$=0.91 min; Mass spectrum (ESI⁺): m/z=284 [M+H]⁺.

Step 2: ({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3-fluorophenyl}imino)dimethyl-λ⁶-sulfanone The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and [(4-bromo-3-fluorophenyl)imino]dimethyl-λ⁶-sulfanone following a procedure analogous to that described for Intermediate 2 (Step 3). LC (method 2): $t_R$=1.13 min; Mass spectrum (ESI⁺): m/z=689 [M+H]⁺.

Intermediate 7

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,3-difluorophenyl}imino)dimethyl-λ⁶-sulfanone

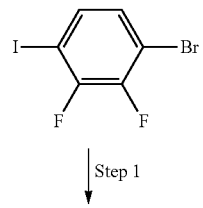

| Step 1

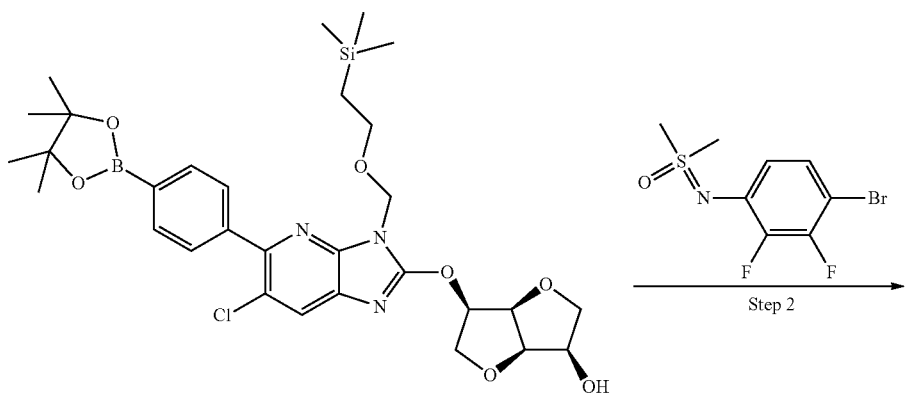

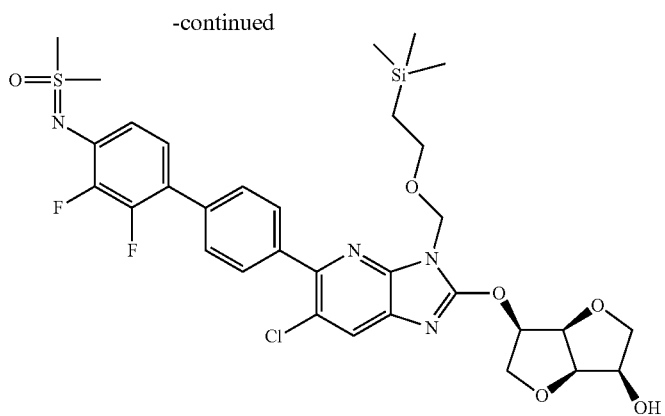

Step 1: [(4-Bromo-2,3-difluorophenyl)imino]dimethyl-λ⁶-sulfanone

The title compound is prepared from 1-bromo-2,3-difluoro-4-iodo-benzene and S,S-dimethylsulfoximine following a procedure analogous to that described for Intermediate 2 (Step 2). LC (method 2): $t_R$=0.93 min; Mass spectrum (ESI⁺): m/z=284 [M+H]⁺.

Step 2: ({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,3-difluorophenyl}imino)dimethyl-λ⁶-sulfanone The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and [(4-bromo-2,3-difluorophenyl)imino]dimethyl-λ⁶-sulfanone following a procedure analogous to that described for Intermediate 2 (Step 3). LC (method 2): $t_R$=1.15 min; Mass spectrum (ESI⁺): m/z=707 [M+H]⁺.

Intermediate 8

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)-3-fluorophenyl]phenyl}-imino)dimethyl-λ⁶-sulfanone

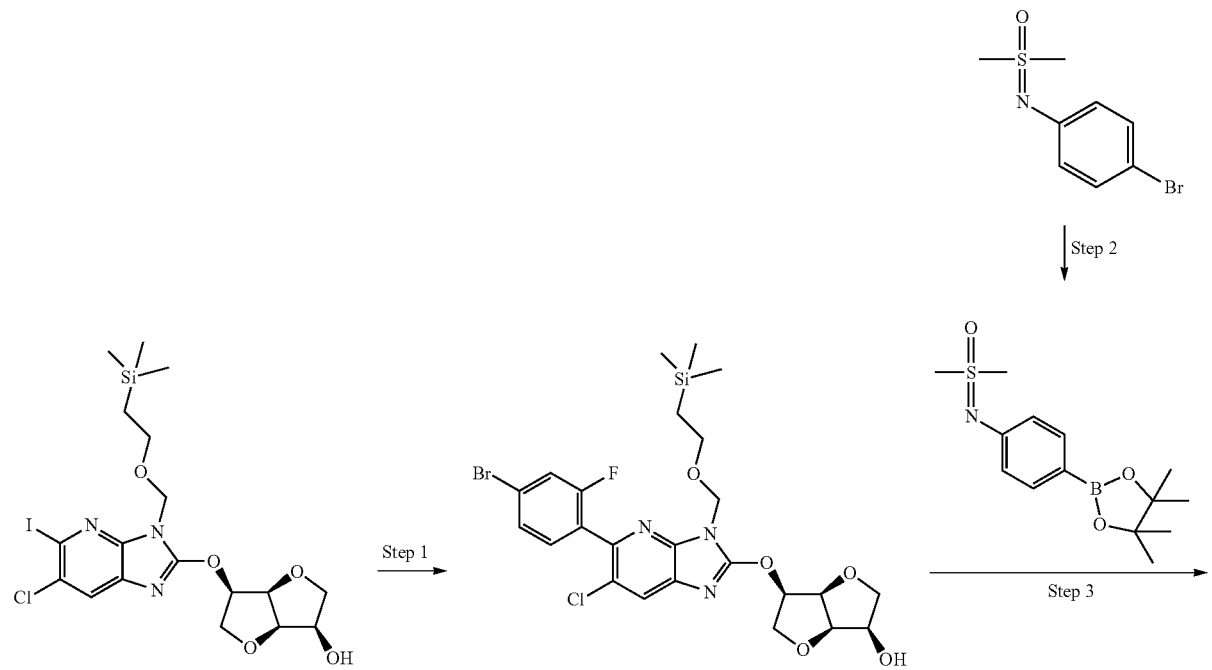

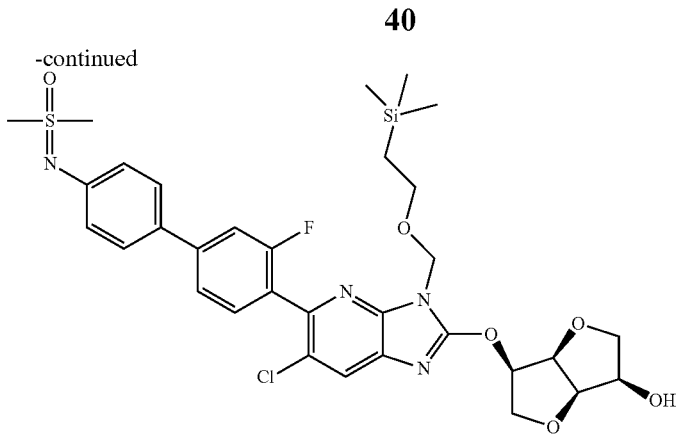

Intermediate 9

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)-2-fluorophenyl]phenyl}-imino)dimethyl-$\lambda^6$-sulfanone

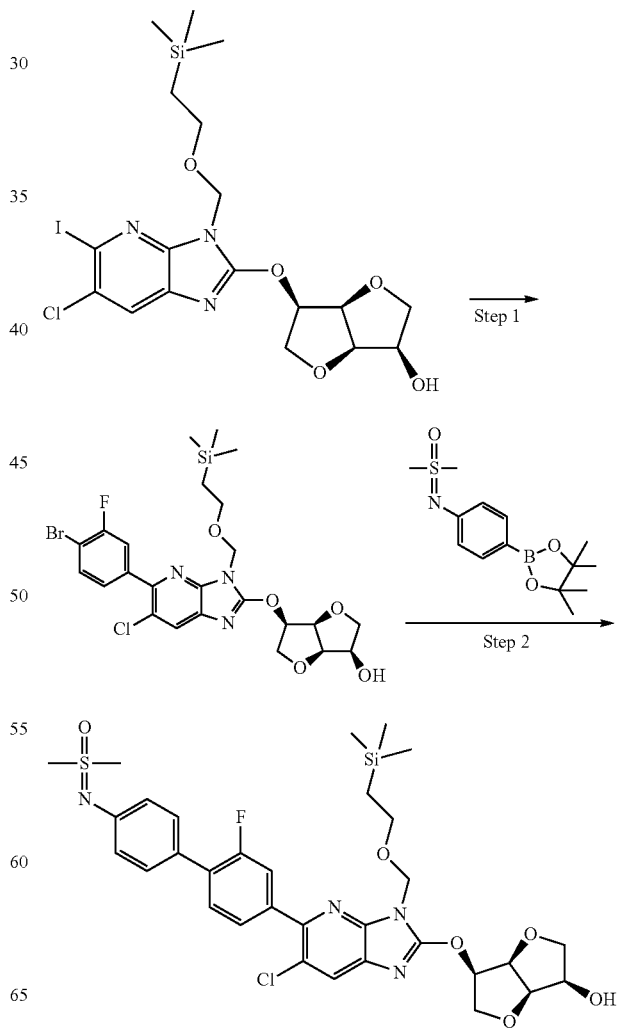

Step 1: (3R,3aR,6R,6aR)-6-{[5-(4-Bromo-2-fluorophenyl)-6-chloro-3-{[2-(trimethylsilyl)ethoxy]methyl}-3H-imidazo[4,5-b]pyridin-2-yl]oxy}-hexahydrofuro[3,2-b]furan-3-ol A mixture of (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol (500 mg), (4-bromo-2-fluorophenyl)boronic acid (220 mg), and aqueous $Na_2CO_3$ solution (2 M, 2.71 mL) in 1,4-dioxane is purged with argon for 5 min. [1,1'-Bis-(diphenylphosphino)-ferrrocen]-dichlorpalladium(II)-$CH_2Cl_2$-complex (37 mg) is added and the mixture is stirred at 90° C. for 4 h. The reaction mixture is diluted with ethyl actate, washed with water and brine, dried over $MgSO_4$, and concentrated in vacuo. The residue is chromatographed on silica gel (cyclohexane/ethyl acetate 50:50→0:100) to give the title compound. LC (method 3): $t_R$=0.94 min; Mass spectrum ($ESI^+$): m/z=600 $[M+H]^+$.

Step 2: Dimethyl({[4-(tetramethyl-1,3,2-dioxaborolan-2-yl)phenyl]imino})-$\lambda^6$-sulfanone A mixture of [(4-bromophenyl)imino]dimethyl-$\lambda^6$-sulfanone (1.58 g), bis(pinacolato)diboron (2.00 g), and $K_2CO_3$ (2.20 g) in 1,4-dioxane is purged with argon for 10 min. [1,1'-Bis-(diphenylphosphino)-ferrrocen]-dichlorpalladium (II)-$CH_2Cl_2$-complex (520 mg) is added and the mixture is stirred overnight at 90° C. After cooling to room temperature the reaction mixture is filtrated, concentrated in vacuo, and submitted to silica gel chromatography (dichloromethane/methanol 99:1→97:3) to give the title compound. LC (method 2): $t_R$=0.96 min; Mass spectrum ($ESI^+$): m/z=296 $[M+H]^+$.

Step 3: ({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)-3-fluorophenyl]phenyl}imino)dimethyl-$\lambda^6$-sulfanone The title compound is prepared from (3R,3aR,6R,6aR)-6-{[5-(4-bromo-2-fluorophenyl)-6-chloro-3-{[2-(trimethylsilyl)ethoxy]methyl}-3H-imidazo[4,5-b]pyridin-2-yl]oxy}-hexahydrofuro[3,2-b]furan-3-ol and dimethyl({[4-(tetramethyl-1,3,2-dioxaborolan-2-yl)phenyl]imino})-$\lambda^6$-sulfanone following a procedure analogous to that described under Step 2. LC (method 2): $t_R$=1.11 min; Mass spectrum ($ESI^+$): m/z=689 $[M+H]^+$.

Step 1: (3R,3aR,6R,6aR)-6-{[5-(4-Bromo-3-fluoro-phenyl)-6-chloro-3-{[2-(trimethyl-silyl)ethoxy]methyl}-3H-imidazo[4,5-b]pyridin-2-yl]oxy}-hexahydrofuro[3,2-b]furan-3-ol The title compound is prepared from (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol and (4-bromo-3-fluorophenyl)boronic acid following a procedure analogous to that described for Intermediate 8 (Step 1). LC (method 3): $t_R$=0.99 min; Mass spectrum (ESI$^+$): m/z=600 [M+H]$^+$.

Step 2: ({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)-2-fluorophenyl]phenyl}imino)dimethyl-$\lambda^6$-sulfanone The title compound is prepared from (3R,3aR,6R,6aR)-6-{[5-(4-bromo-3-fluorophenyl)-6-chloro-3-{[2-(trimethylsilyl)ethoxy]methyl}-3H-imidazo[4,5-b]pyridin-2-yl]oxy}-hexahydrofuro[3,2-b]furan-3-ol and dimethyl({[4-(tetramethyl-1,3,2-dioxaborolan-2-yl)phenyl]imino})-$\lambda^6$-sulfanone following a procedure analogous to that described for Intermediate 8 (Step 3). LC (method 2): $t_R$=1.18 min; Mass spectrum (ESI$^+$): m/z=689 [M+H]$^+$.

Intermediate 10

({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)-2,3-difluorophenyl]-phenyl}imino)dimethyl-$\lambda^6$-sulfanone

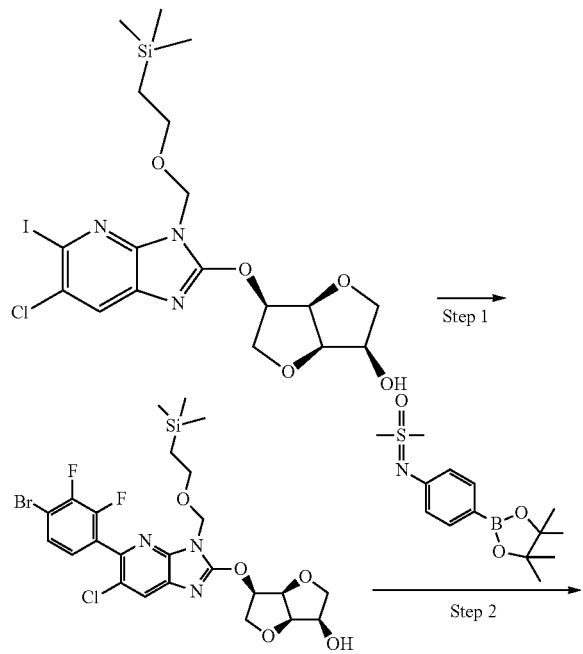

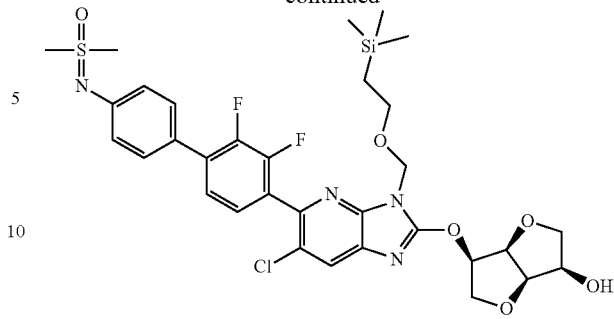

Step 1: (3R,3aR,6R,6aR)-6-{[5-(4-Bromo-2,3-difluorophenyl)-6-chloro-3-{[2-(trimethylsilyl)ethoxy]methyl}-3H-imidazo[4,5-b]pyridin-2-yl]oxy}-hexahydrofuro[3,2-b]furan-3-ol The title compound is prepared from (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol and (4-bromo-2,3-difluorophenyl)boronic acid following a procedure analogous to that described for Intermediate 8 (Step 1). LC (method 3): $t_R$=0.96 min; Mass spectrum (ESI$^+$): m/z=618 [M+H]$^+$.

Step 2: ({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}imidazo[4,5-b]pyridin-5-yl)-2,3-difluorophenyl]phenyl}imino)dimethyl-$\lambda^6$-sulfanone The title compound is prepared from (3R,3aR,6R,6aR)-6-{[5-(4-bromo-2,3-difluorophenyl)-6-chloro-3-{[2-(trimethylsilyl)ethoxy]methyl}-3H-imidazo[4,5-b]pyridin-2-yl]oxy}-hexahydrofuro[3,2-b]furan-3-ol and dimethyl({[4-(tetramethyl-1,3,2-dioxaborolan-2-yl)phenyl]imino})-$\lambda^6$-sulfanone following a procedure analogous to that described for Intermediate 8 (Step 3). LC (method 2): $t_R$=1.13 min; Mass spectrum (ESI$^+$): m/z=707 [M+H]$^+$.

Intermediate 11

({6-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-5-fluoropyridin-3-yl}imino)dimethyl-$\lambda^6$-sulfanone

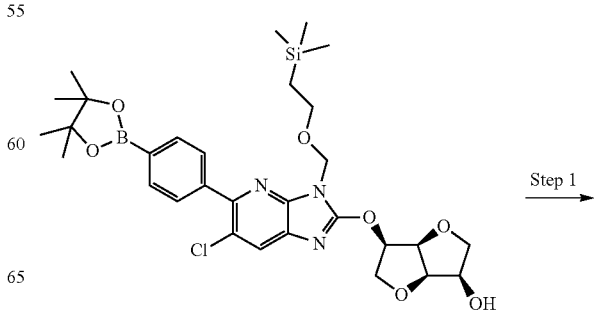

-continued

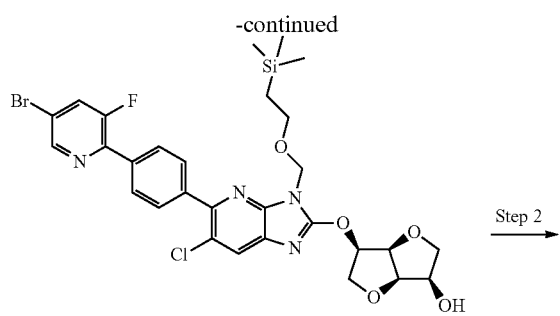

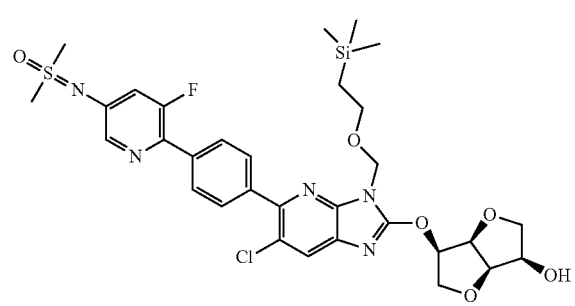

Step 1: ((3R,3aR,6R,6aR)-6-({5-[4-(5-Bromo-3-fluoropyridin-2-yl)phenyl]-6-chloro-3-{[2-(trimethylsilyl)ethoxy]methyl}-3H-imidazo[4,5-b]pyridin-2-yl}oxy)-hexahydrofuro-[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 5-bromo-3-fluoro-2-iodo-pyridine following a procedure analogous to that described for Intermediate 2 (Step 3). LC (method 2): $t_R$=1.32 min; Mass spectrum (ESI$^+$): m/z=677 [M+H]$^+$.

Step 2: ({6-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-5-fluoropyridin-3-yl}imino) dimethyl-λ$^6$-sulfanone The title compound is prepared from ((3R,3aR,6R,6aR)-6-({5-[4-(5-bromo-3-fluoropyridin-2-yl)phenyl]-6-chloro-3-{[2-(trimethylsilyl)ethoxy]methyl}-3H-imidazo[4,5-b]pyridin-2-yl}oxy)-hexahydrofuro[3,2-b]furan-3-ol and S,S-dimethylsulfoximine following a procedure analogous to that described for Intermediate 2 (Step 2). LC (method 2): $t_R$=1.09 min; Mass spectrum (ESI$^+$): m/z=690 [M+H]$^+$.

Intermediate 12

({4-[5-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)-6-methoxypyridin-2-yl]phenyl}imino) dimethyl-λ$^6$-sulfanone

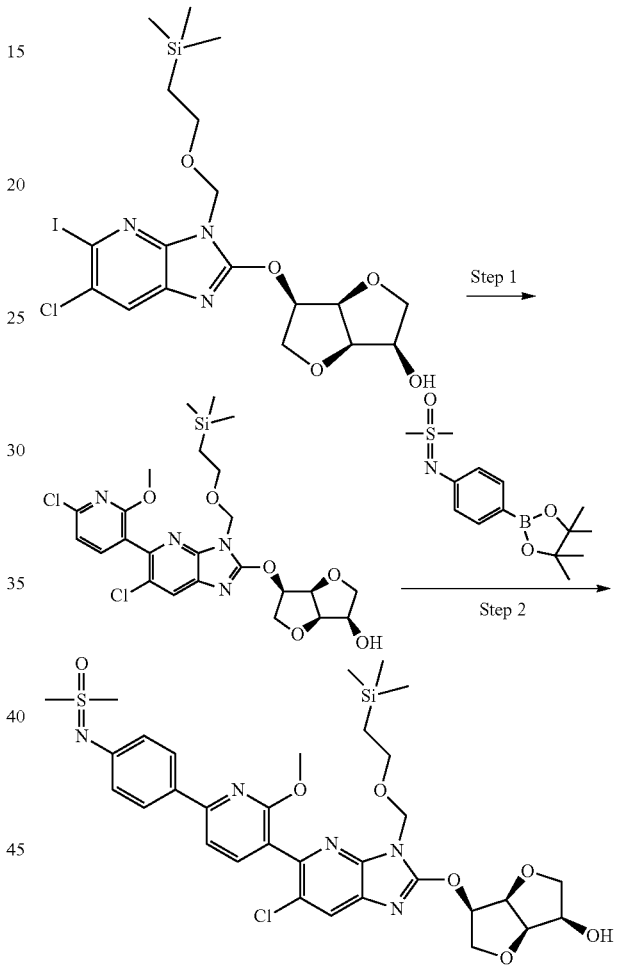

Step 1: (3R,3aR,6R,6aR)-6-{[6-Chloro-5-(6-chloro-2-methoxypyridin-3-yl)-3-{[2-(trimethylsilyl)ethoxy]methyl}-3H-imidazo[4,5-b]pyridin-2-yl]oxy}-hexahydrofuro[3,2-b]furan-3-ol The title compound is prepared from (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol and (6-chloro-2-methoxypyridin-3-yl)boronic acid following a procedure analogous to that described for Intermediate 8 (Step 1). LC (method 2): $t_R$=1.25 min; Mass spectrum (ESI$^+$): m/z=569 [M+H]$^+$.

Step 2: ({4-[5-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)-6-methoxypyridin-2-yl]phenyl}imino)dimethyl-λ⁶-sulfanone The title compound is prepared from (3R,3aR,6R,6aR)-6-{[6-chloro-5-(6-chloro-2-methoxypyridin-3-yl)-3-{[2-(trimethylsilyl)ethoxy]methyl}-3H-imidazo[4,5-b]pyridin-2-yl]oxy}-hexahydrofuro[3,2-b]furan-3-ol and dimethyl({[4-(tetramethyl-1,3,2-dioxaborolan-2-yl)phenyl]imino})-λ⁶-sulfanone following a procedure analogous to that described for Intermediate 8 (Step 3). LC (method 2): $t_R$=1.10 min; Mass spectrum (ESI⁺): m/z=702 [M+H]⁺.

Intermediate 13

({4-[4-(2-{[(3R,3aR,6R,6aR)-6-Hydroxy-hexahydrofuro[3,2-b]furan-3-yl]oxy}-6-fluoro-1-{[2-(trimethylsilyl)ethoxy]methyl}-1H-imidazo[4,5-b]pyridin-5-yl)phenyl]phenyl}-imino)dimethyl-λ⁶-sulfanone

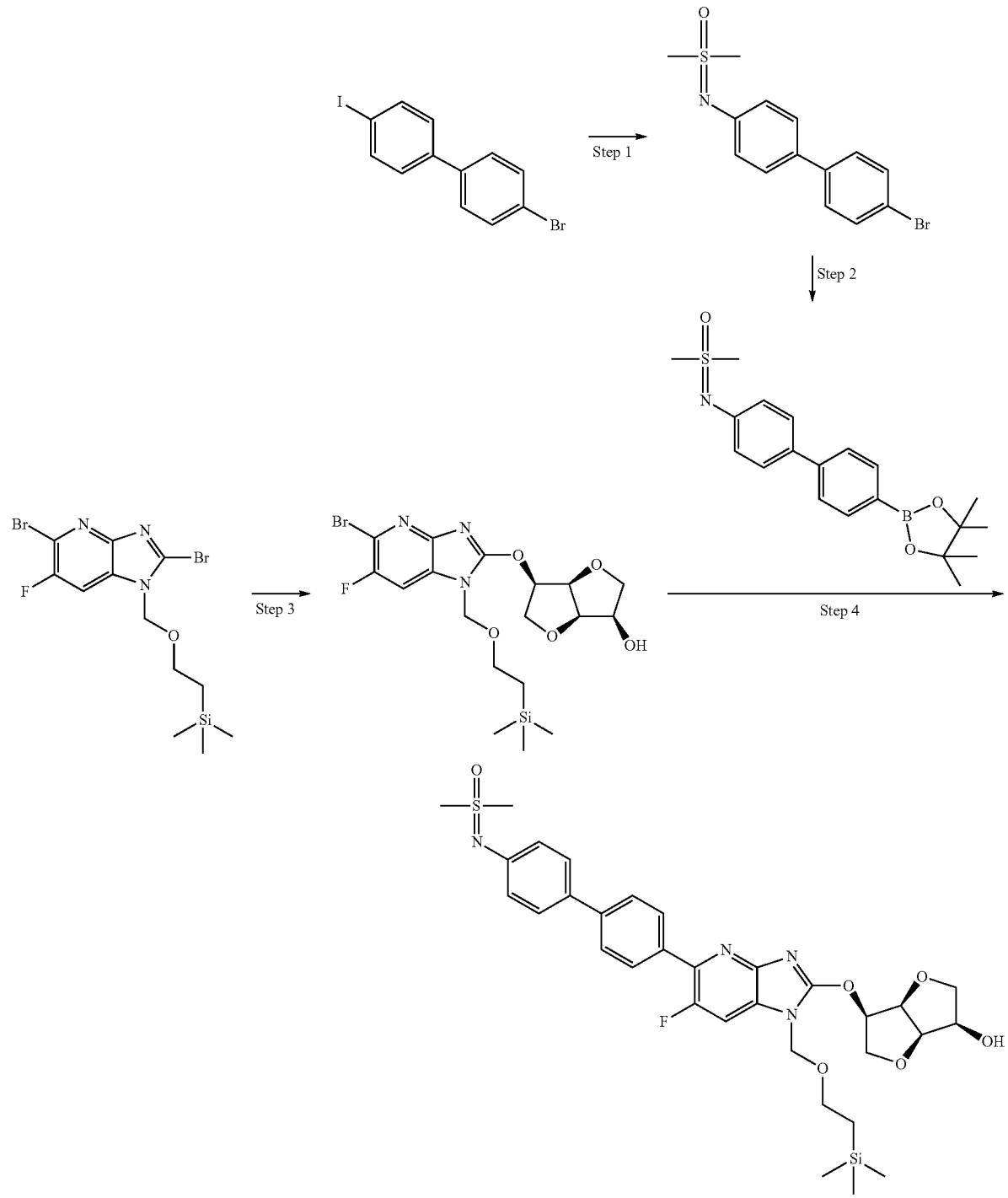

Step 1: {[4-(4-Bromophenyl)phenyl]imino}dimethyl-λ⁶-sulfanone

The title compound is prepared from 4-bromo-4'-iodobiphenyl and S,S-dimethylsulfoximine following a procedure analogous to that described for Intermediate 2 (Step 2). LC (method 5): $t_R$=0.98 min; Mass spectrum (ESI⁺): m/z=284 [M+H]⁺.

Step 2: Dimethyl({4-[4-(tetramethyl-1,3,2-dioxaborolan-2-yl)phenyl]phenyl}imino)-λ⁶-sulfanone The title compound is prepared from {[4-(4-bromophenyl)phenyl]imino}dimethyl-λ⁶-sulfanone and bis(pinacolato)diboron following a procedure analogous to that described for Intermediate 8 (Step 2). LC (method 5): $t_R$=1.01 min; Mass spectrum (ESI⁺): m/z=372 [M+H]⁺.

Step 3: (3R,3aR,6R,6aR)-6-[(5-Bromo-6-fluoro-1-{[2-(trimethylsilyl)ethoxy]methyl}-1H-imidazo[4,5-b]pyridin-2-yl)oxy]-hexahydrofuro[3,2-b]furan-3-ol Potassium tert-butoxide (217 mg) is added to an ice-cooled mixture of isomannide (282 mg) and 5-bromo-2-chloro-6-fluoro-1-{[2-(trimethylsilyl)ethoxy]methyl}-1H-imidazo[4,5-b]pyridine (WO 2013/011932, p. 82-83; 490 mg) in tetrahydrofuran (20 mL) under an argon atmosphere. The resulting mixture is stirred at room temperature for 2 d. Ethyl acetate is added and the mixture is washed with water and brine, dried over MgSO₄ and concentrated in vacuo. The residue is chromatographed on silica gel (dichloromethane/methanol 97:3→80:20) to give the title compound. LC (method 1): $t_R$=1.07 min; Mass spectrum (ESI⁺): m/z=490 [M+H]⁺.

Step 4: ({4-[4-(2-{[(3R,3aR,6R,6aR)-6-Hydroxy-hexahydrofuro[3,2-b]furan-3-yl]oxy}-6-fluoro-1-{[2-(trimethylsilyl)ethoxy]methyl}-1H-imidazo[4,5-b]pyridin-5-yl)phenyl]phenyl}imino)dimethyl-λ⁶-sulfanone A mixture of (3R,3aR,6R,6aR)-6-[(5-bromo-6-fluoro-1-{[2-(trimethylsilyl)ethoxy]-methyl}-1H-imidazo[4,5-b]pyridin-2-yl)oxy]-hexahydrofuro[3,2-b]furan-3-ol (150 mg), dimethyl({4-[4-(tetramethyl-1,3,2-dioxaborolan-2-yl)phenyl]phenyl}imino)-λ⁶-sulfanone (136 mg), and aqueous Na₂CO₃ solution (2 M, 0.61 mL) in N,N-dimethylformamide (6 mL) is purged with argon for several minutes. Bis(di-tert-butyl(4-dimethylaminophenyl)phosphine)dichloropalladium(II) (13 mg) is added and the mixture is stirred at 70° C. for 3 h. The reaction mixture is allowed to cool to room temperature, diluted with water, and extracted with ethyl acetate. The combined extracts are washed with brine, dried over MgSO₄, and concentrated in vacuo. The crude product is purified by column chromatography on silica gel (ethyl acetate/methanol 95:5→70:30) to give the title compound. LC (method 1): $t_R$=1.07 min; Mass spectrum (ESI⁺): m/z=655 [M+H]⁺.

Intermediate 14

{4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3-fluorophenyl}(imino)methyl-λ⁶-sulfanone

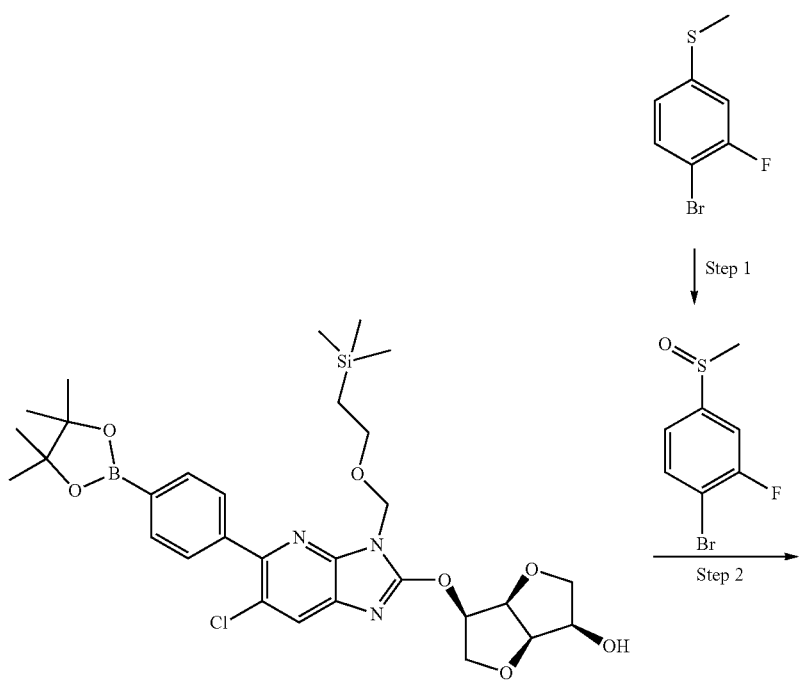

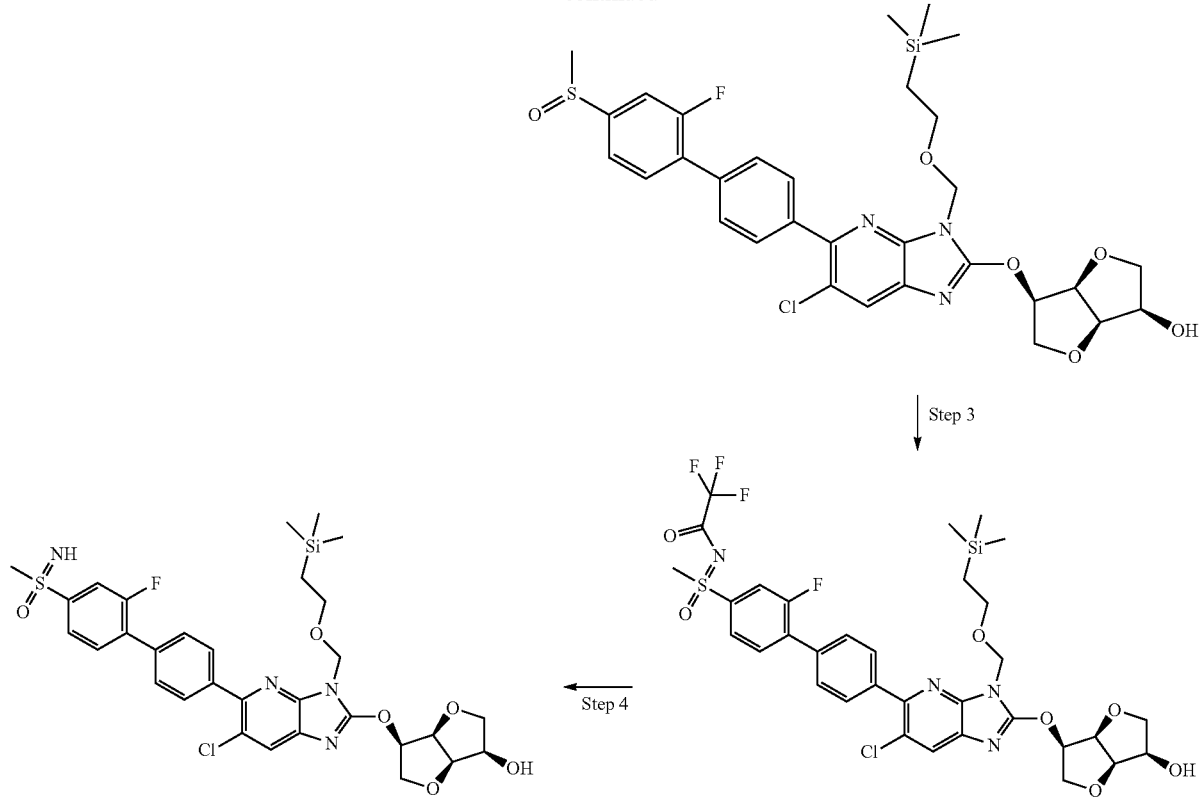

Step 1: 1-Bromo-2-fluoro-4-methanesulfinylbenzene

3-Chloroperoxybenzoic acid id added slowly to an ice-cooled solution of 4-bromo-3-fluorothioanisole (1.00 g) in and the resulting mixture is stirred for 1 h. The ice bath is removed and the mixture is stirred for 2 h at room temperature. The reaction mixture is diluted with dichloromethane (20 mL), washed with a saturated aqueous solution of NaHCO$_3$ and water, dried over MgSO$_4$, and concentrated in vacuo. The crude product is used for the next reaction step without further purification. Mass spectrum (ESI$^+$): m/z=237 [M+H]$^+$.

Step 2: (3R,3aR,6R,6aR)-6-({6-Chloro-5-[4-(2-fluoro-4-methanesulfinylphenyl)phenyl]-3-{[2-(trimethylsilyl)ethoxy]methyl}-3H-imidazo[4,5-b]pyridin-2-yl}oxy)-hexahydrofuro[3,2-b]furan-3-ol The title compound is prepared from (3R,3aR,6R,6aR)-6-(6-chloro-5-(4-(4,4,5,5-tetramethyl-1,3,2-dioxaborolan-2-yl)phenyl)-3-(2-trimethylsilanyl-ethoxymethyl)-3H-imidazo[4,5-b]pyridin-2-yloxy)hexahydrofuro[3,2-b]furan-3-ol and 1-bromo-2-fluoro-4-methanesulfinylbenzene following a procedure analogous to that described for Intermediate 2 (Step 3). LC (method 2): t$_R$=1.14 min; Mass spectrum (ESI$^+$): m/z=284 [M+H]$^+$.

Step 3: N-({4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3-fluorophenyl}(methyl)oxo-λ$^6$-sulfanylidene)-2,2,2-trifluoroacetamide A mixture of (3R,3aR,6R,6aR)-6-({6-chloro-5-[4-(2-fluoro-4-methanesulfinyl-phenyl)phenyl]-3-{[2-(trimethylsilyl)ethoxy]methyl}-3H-imidazo[4,5-b]pyridin-2-yl}oxy)-hexahydrofuro[3,2-b]furan-3-ol (200 mg), 2,2,2-trifluoroacetamide (68 mg), iodobenzene diacetate (146 mg), magnesium oxide (49 mg), and rhodium(II) acetate dimer (3 mg) in dichloromethane (2 mL) is stirred overnight at room temperature. The reaction mixture is diluted with dichloromethane and filtered. The filtrate is washed with water and brine, dried over MgSO$_4$, and concentrated in vacuo. The crude product is used in the next reaction step without further purification. LC (method 2): t$_R$=1.23 min; Mass spectrum (ESI$^+$): m/z=771 [M+H]$^+$.

Step 4: {4-[4-(2-{[(3R,3aR,6R,6aR)-6-Hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3-fluorophenyl}(imino)methyl-λ$^6$-sulfanone A mixture of N-({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3-fluorophenyl}(methyl)oxo-λ$^6$-sulfanylidene)-2,2,2-trifluoroacetamide (217 mg) and potassium carbonate (130 mg) in methanol (4 mL) is stirred at room temperature for 2 h. The reaction mixture is diluted with dichloromethane, washed with water, dried over MgSO$_4$, and concentrated in vacuo. The crude product is used in the next reaction step without further purification. LC (method 2): t$_R$=1.06 min; Mass spectrum (ESI$^+$): m/z=675 [M+H]$^+$.

51

Intermediate 15

({4-[4-(2-{[(3R,3aR,6R,6aR)-6-Hydroxy-hexahydrofuro[3,2-b]furan-3-yl]oxy}-6-fluoro-1-{[2-(trimethylsilyl)ethoxy]methyl}-1H-imidazo[4,5-b]pyridin-5-yl)phenyl]-3-fluorophenyl}imino)dimethyl-λ$^6$-sulfanone

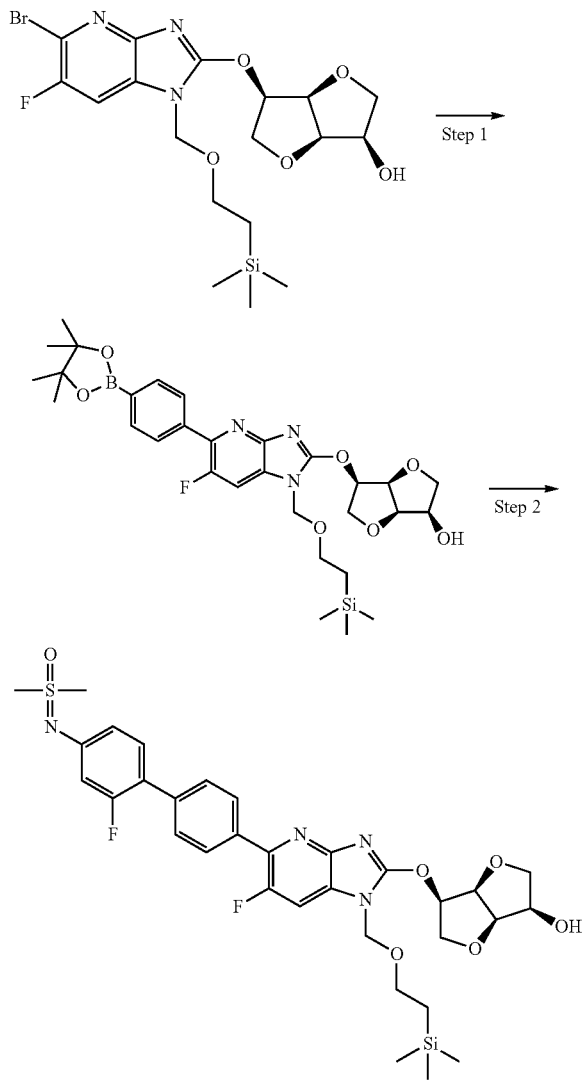

52

Step 1: (3R,3aR,6R,6aR)-6-({6-Fluoro-5-[4-(tetramethyl-1,3,2-dioxaborolan-2-yl)phenyl]-1-{[2-(trimethylsilyl)ethoxy]methyl}-1H-imidazo[4,5-b]pyridin-2-yl}oxy)-hexahydrofuro[3,2-b]furan-3-ol The title compound is prepared from (3R,3aR,6R,6aR)-6-[(5-bromo-6-fluoro-1-{[2-(trimethylsilyl)ethoxy]methyl}-1H-imidazo[4,5-b]pyridin-2-yl)oxy]-hexahydrofuro[3,2-b]furan-3-ol and 1,4-benzenediboronic acid dipinacol ester following a procedure analogous to that described for Intermediate 2 (Step 1). LC (method 3): $t_R$=0.92 min; Mass spectrum (ESI$^+$): m/z=614 [M+H]$^+$.

Step 2: ({4-[4-(2-{[(3R,3aR,6R,6aR)-6-Hydroxy-hexahydrofuro[3,2-b]furan-3-yl]oxy}-6-fluoro-1-{[2-(trimethylsilyl)ethoxy]methyl}-1H-imidazo[4,5-b]pyridin-5-yl)phenyl]-3-fluorophenyl}imino)dimethyl-λ$^6$-sulfanone The title compound is prepared from (3R,3aR,6R,6aR)-6-({6-fluoro-5-[4-(tetramethyl-1,3,2-dioxaborolan-2-yl)phenyl]-1-{[2-(trimethylsilyl)ethoxy]methyl}-1H-imidazo[4,5-b]pyridin-2-yl}oxy)-hexahydrofuro[3,2-b]furan-3-ol and [(4-bromo-3-fluorophenyl)-imino]dimethyl-λ$^6$-sulfanone following a procedure analogous to that described for Intermediate 2 (Step 3). LC (method 2): $t_R$=1.13 min; Mass spectrum (ESI$^+$): m/z=284 [M+H]$^+$.

Intermediate 16

({4-[5-(2-{[(3R,3aR,6R,6aR)-6-Hydroxy-hexahydrofuro[3,2-b]furan-3-yl]oxy}-6-chloro-imidazo[4,5-b]pyridin-5-yl)-6-methoxypyridin-2-yl]-3-fluorophenyl}imino)dimethyl-λ$^6$-sulfanone

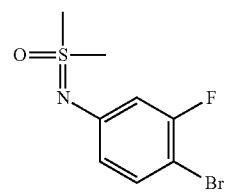

↓ Step 1

-continued

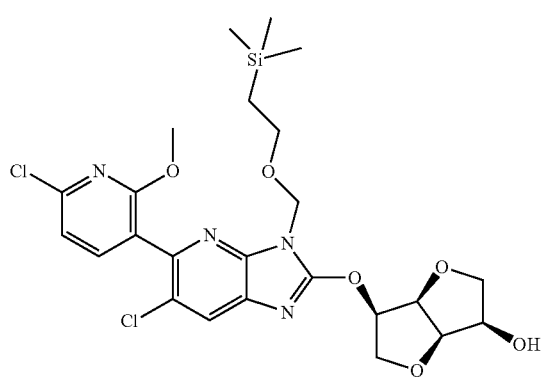
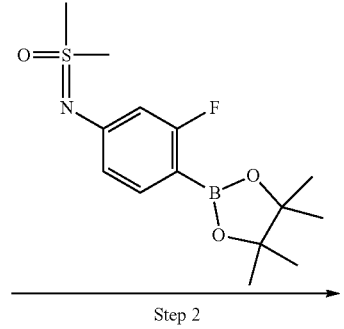

Step 2

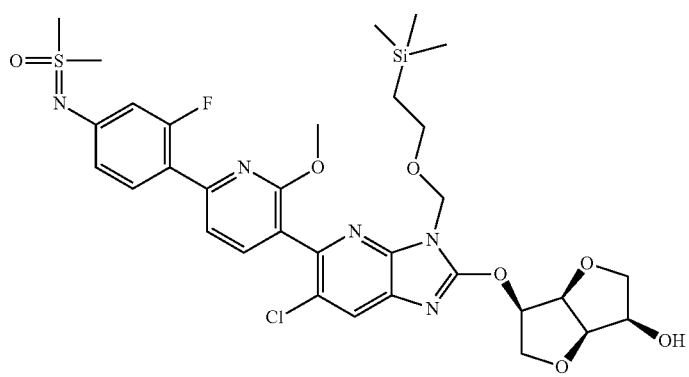

Step 1: {[3-Fluoro-4-(tetramethyl-1,3,2-dioxaborolan-2-yl)phenyl]imino}dimethyl-$\lambda^6$ sulfanone The title compound is prepared from [(4-bromo-3-fluorophenyl)imino]dimethyl-$\lambda^6$ sulfanone and bis(pinacolato)diboron following a procedure analogous to that described for Intermediate 8 (Step 2). LC (method 2): $t_R$=0.98 min; Mass spectrum (ESI$^+$): m/z=314 [M+H]$^+$.

Step 2: ({4-[5-(2-{[(3R,3aR,6R,6aR)-6-Hydroxyhexahydrofuro[3,2-b]furan-3-yl]oxy}-6-chloro-3H-imidazo[4,5-b]pyridin-5-yl)-6-methoxypyridin-2-yl]-3-fluorophenyl}imino)dimethyl-$\lambda^6$-sulfanone The title compound is prepared from (3R,3aR,6R,6aR)-6-{[6-chloro-5-(6-chloro-2-methoxypyridin-3-yl)-3-{[2-(trimethylsilyl)ethoxy]methyl}-3H-imidazo[4,5-b]pyridin-2-yl]oxy}-hexahydrofuro[3,2-b]furan-3-ol and {[3-fluoro-4-(tetramethyl-1,3,2-dioxaborolan-2-yl)phenyl]imino}dimethyl-$\lambda^6$-sulfanone following a procedure analogous to that described for Intermediate 8 (Step 3). LC (method 2): $t_R$=1.13 min; Mass spectrum (ESI$^+$): m/z=720 [M+H]$^+$.

Intermediate 17

{[4-(4-Bromo-3,5-difluorophenyl)phenyl]imino}dimethyl-$\lambda^6$-sulfanone

Aqueous Na$_2$CO$_3$ solution (2 M, 4.30 mL) is added to mixture of dimethyl({[4-(tetramethyl-1,3,2-dioxaborolan-2-yl)phenyl]imino})-λ$^6$-sulfanone (1.00 g) and 4-bromo-3,5-difluoroiodobenzene (1.30 g) in 1,4-dioxane (10 mL) and the resulting mixture is purged with argon for several minutes. [1,1'-Bis-(diphenylphosphino)-ferrrocen]-dichlorpalladium (II)-CH$_2$Cl$_2$-complex (277 mg) is added and the mixture is stirred overnight at 80° C. The reaction mixture is diluted with 30 mL of water and 30 mL of ethyl acetate and filtered. The aqueous phase is separated and extracted with 30 mL of ethyl acetate. The combined organic phases are washed with water and brine, dried over MgSO$_4$ and concentrated in vacuo. The crude product is purified by column chromatography on silica gel (cyclohexane/ethyl acetate 50:50→0:100) to give the title compound. LC (method 2): t$_R$=1.09 min; Mass spectrum (ESI$^+$): m/z=284 [M+H]$^+$.

Intermediate 18

({4-[4-(2-{[(3R,3aR,6R,6aS)-6-[(tert-Butyldimethyl-silyl)oxy]-hexahydrofuro[3,2-b]furan-3-yl]oxy}-6-chloro-3-{[2-(trimethylsilyl)ethoxy]methyl}imidazo[4,5-b]pyridin-5-yl)-3,5-difluorophenyl]phenyl}imino)dimethyl-λ$^6$-sulfanone

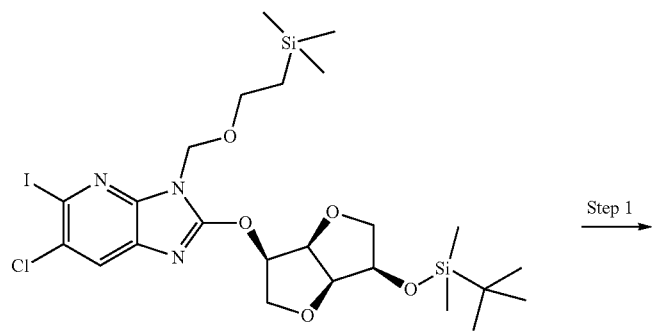

Step 1

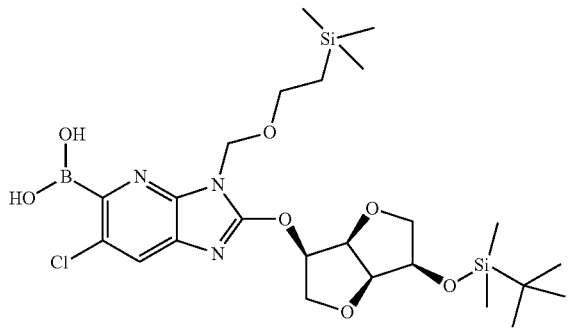

Step 2

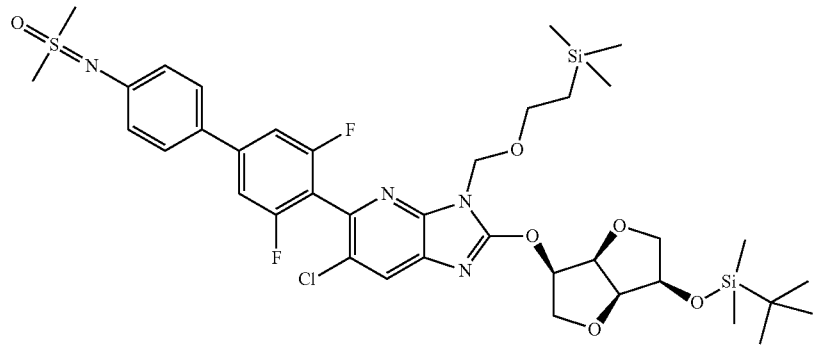

Step 1: 2-{[(3R,3aR,6R,6aS)-6-[(tert-Butyldimethyl-silyl)oxy]-hexahydrofuro[3,2-b]furan-3-yl]oxy}-6-chloro-3-{[2-(trimethylsilyl)ethoxy]methyl}imidazo[4,5-b]pyridin-5-ylboronic Acid Isopropylmagensium chloride-lithium chloride complex (1.3 M, 1.27 mL) is added drop wise to a stirred solution of (3R,3aR,6R,6aR)-6-(6-chloro-5-iodo-3-(2-trimethylsilanyl-ethoxymethyl)-3H-imidazo[4,5-b]pyridin-2-yloxy)hexahydrofuro[3,2-b]furan-3-ol (1.00 g) in tetrahydrofuran (10 mL) cooled in an acetone/dry ice bath under an argon atmosphere. After 30 min a solution of 2-isopropoxy-4,4,5,5-tetramethyl-1,3,2-dioxoborolane (0.35 g) in tetrahydrofuran (3 mL) is added drop wise and the resulting mixture is stirred for 1 h. The cooling bath is removed and the reaction mixture is stirred overnight at room temperature. The reaction is quenched with aqueous ammonium chloride solution (10%) and extracted with ethyl acetate. The combined extracts are concentrated in vacuo and the crude product is used in the next reaction step without further purification. LC (method 2): $t_R$=1.00 min; Mass spectrum (ESI$^+$): m/z=586 [M+H]$^+$.

Step 2: ({4-[4-(2-{[(3R,3aR,6R,6aS)-6-[(tert-Butyldimethylsilyl)oxy]-hexahydrofuro[3,2-b]furan-3-yl]oxy}-6-chloro-3-{[2-(trimethylsilyl)ethoxy]methyl}imidazo[4,5-b]pyridin-5-yl)-3,5-difluorophenyl]phenyl]imino)dimethyl-λ$^6$-sulfanone Aqueous potassium phosphate solution (0.5 M; 0.68 mL) is added to a mixture of {[4-(4-bromo-3,5-difluorophenyl)phenylhenyl]imino}dimethyl-λ$^6$-sulfanone (74 mg) and 2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}imidazo[4,5-b]pyridin-5-ylboronic acid (100 mg) in 1,4-dioxane (3 mL) in a microwave vial and the resulting mixture is purged with argon for 1 min. Chloro(2-dicyclohexylphosphino-2',4',6'-triisopropyl-1,1'-biphenyl)[2-(2'-amino-1,1'-biphenyl)]palladium(II) (6.71 mg) is added, the mixture is again purged with argon, the vial is capped, and the reaction mixture is stirred for 1 h at room temperature. After standing overnight ethyl acetate and water are added and the organic phase is separated, washed with water and brine, dried over MgSO$_4$, and concentrated in vacuo. The residue is chromatographed on silica gel (cyclohexane/ethyl acetate 50:50→20:80) to give the title compound. LC (method 3): $t_R$=1.19 min; Mass spectrum (ESI$^+$): m/z=821 [M+H]$^+$.

Intermediate 19

({4-[4-(2-{[(3R,3aR,6R,6aS)-6-[(tert-Butyldimethyl-silyl)oxy]-hexahydrofuro[3,2-b]furan-3-yl]oxy}-6-fluoro-3-{[2-(trimethylsilyl)ethoxy]methyl}imidazo[4,5-b]pyridin-5-yl)-3,5-difluorophenyl]phenyl}imino)dimethyl-λ$^6$-sulfanone

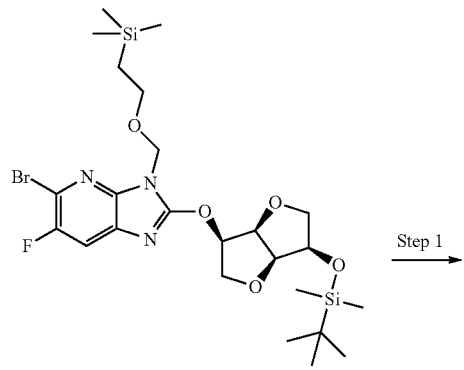

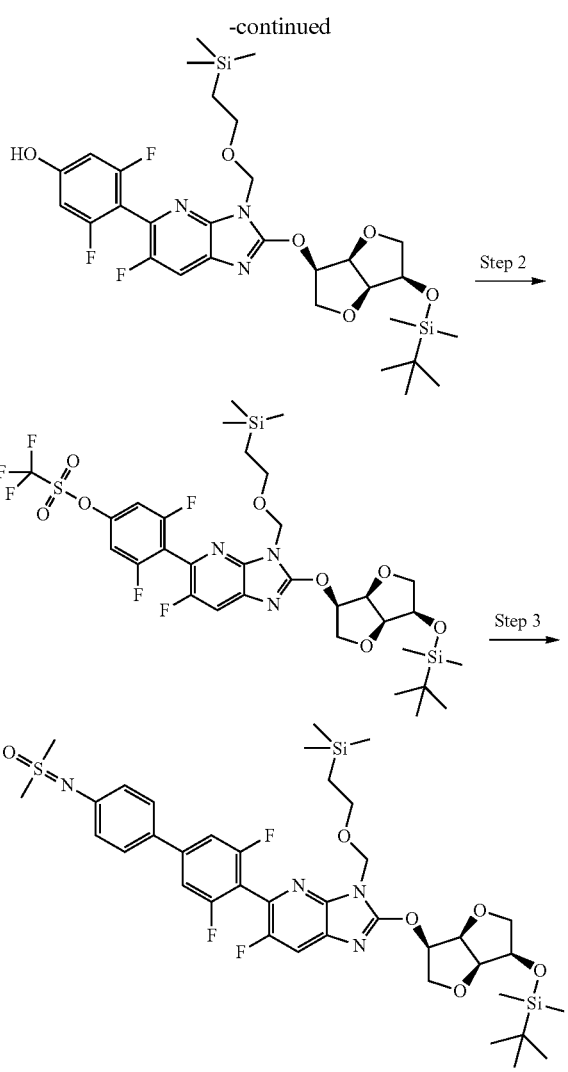

Step 1: 4-(2-{[(3R,3aR,6R,6aS)-6-[(tert-Butyldim-ethylsilyl)oxy]-hexahydrofuro[3,2-b]furan-3-yl]oxy}-6-fluoro-3-{[2-(trimethylsilyl)ethoxy]methyl}imidazo[4,5-b]pyridin-5-yl)-3,5-difluorophenol The title compound is prepared from 2-{[(3R,3aR,6R,6aS)-6-[(tert-butyldimethylsilyl)oxy]-hexahydrofuro[3,2-b]furan-3-yl]oxy}-5-bromo-6-fluoro-3-{[2-(trimethylsilyl)ethoxy]methyl}imidazo[4,5-b]pyridine and 2,6-difluoro-4-hydroxy-phenylboronic acid following a procedure analogous to that described for Intermediate 18 (Step 2). LC (method 3): $t_R$=1.20 min; Mass spectrum (ESI$^+$): m/z=284 [M+H]$^+$. Step 2: 4-(2-{[(3R,3aR,6R,6aS)-6-[(tert-Butyldim-ethylsilyl)oxy]-hexahydrofuro[3,2-b]furan-3-yl]oxy}-6-fluoro-3-{[2-(trimethylsilyl)ethoxy]methyl}imidazo[4,5-b]pyridin-5-yl)-3,5-difluorophenyl trifluoromethanesulfonate Trifluoromethansulfonic anhydride (1 M in dichloromethane; 0.18 mL) is added to 4-(2-{[(3R,3aR,6R,6aS)-6-[(tert-butyldimethylsilyl)oxy]-hexahydrofuro[3,2-b]furan-3-yl]oxy}-6-fluoro-3-{[2-(trimethylsilyl)ethoxy]methyl}imidazo[4,5-b]pyridin-5-yl)-3,5-difluorophenol (100 mg) in dichloromethane (2 mL) at 0° C. and the resulting mixture is stirred at this temperature for 1 h. The reaction mixture is diluted with dichloromethane and aqueous ammonium chloride solution (10%). The organic phase is separated, washed with aqueous ammonium chloride solution (10%), dried over MgSO$_4$, and concentrated in vacuo. The crude product is used without further purification for the next reaction step. LC (method 3): $t_R$=1.32 min; Mass spectrum (ESI$^+$): m/z=786 [M+H]$^+$.

Step 3: ({4-[4-(2-{[(3R,3aR,6R,6aS)-6-[(tert-Butyldimethylsilyl)oxy]-hexahydrofuro[3,2-b]furan-3-yl]oxy}-6-fluoro-3-{[2-(trimethylsilyl)ethoxy]methyl}imidazo[4,5-b]pyridin-5-yl)-3,5-difluorophenyl]phenyl}imino)dimethyl-λ$^6$-sulfanone The title compound is prepared from 4-(2-{[(3R,3aR,6R,6aS)-6-[(tert-butyldimethylsilyl)oxy]-hexahydrofuro[3,2-b]furan-3-yl]oxy}-6-fluoro-3-{[2-(trimethyl-silyl)ethoxy]methyl}imidazo[4,5-b]pyridin-5-yl)-3,5-difluorophenyl trifluoromethanesulfonate and dimethyl({[4-(tetramethyl-1,3,2-dioxaborolan-2-yl)phenyl]imino})-λ$^6$-sulfanone following a procedure analogous to that described for Intermediate 8 (Step 3). LC (method 3): $t_R$=1.17 min.

Example 1

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-2-fluorophenyl}imino)dimethyl-λ$^6$-sulfanone

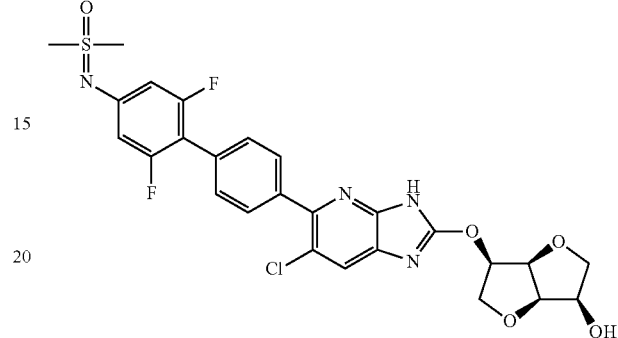

A mixture of ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2-fluorophenyl}imino)dimethyl-λ$^6$-sulfanone (37 mg) and KHSO$_4$ (2 M aqueous solution, 27 μL) in formic acid (1 mL) is stirred for 2 h at 65° C. The mixture is cooled to 0° C. in an ice bath, the pH is adjusted to 11 by adding NaOH (10 M aqueous solution) and the mixture is stirred for 1.5 h. Hydrochloric acid (4 N) is added until the pH reaches 6. The mixture is diluted with water and the precipitate is filtered off and washed with water. The solid residue is rinsed from the filter with 1,4-dioxane and the solvent is removed by freeze drying to give the title compound. LC (method 2): $t_R$=0.89 min; Mass spectrum (ESI$^+$): m/z=559 [M+H]$^+$.

Example 2

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-3,5-difluorophenyl}imino)dimethyl-λ$^6$-sulfanone

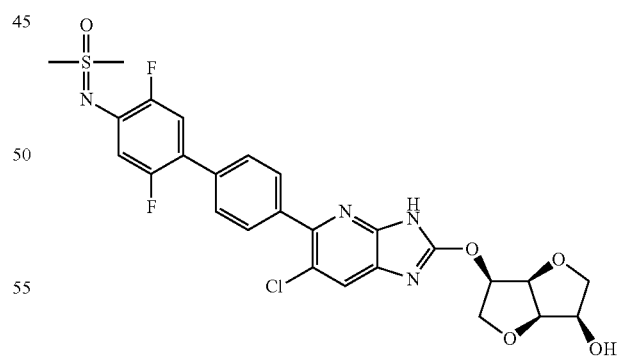

The title compound is prepared from ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3,5-difluorophenyl}imino)dimethyl-λ$^6$-sulfanone following a procedure analogous to that described for Example 1. LC (method 2): $t_R$=0.92 min; Mass spectrum (ESI$^+$): m/z=577 [M+H]$^+$.

Example 3

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-2,5-difluorophenyl}imino)dimethyl-λ$^6$-sulfanone The title compound is prepared from ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,5-difluorophenyl}imino)dimethyl-λ$^6$-sulfanone following a procedure analogous to that described for Example 1. LC (method 2): $t_R$=0.91 min; Mass spectrum (ESI$^+$): m/z=577 [M+H]$^+$.

Example 4

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-2,6-difluorophenyl}imino)dimethyl-$\lambda^6$-sulfanone

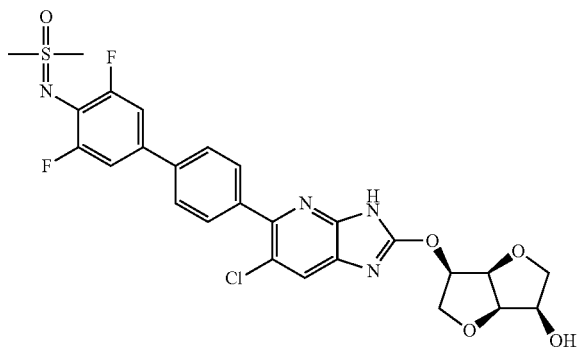 [SMILES: CS(C)(=O)=Nc1c(F)cc(-c2ccc(-c3nc4[nH]c(O[C@@H]5CO[C@H]6[C@@H]5OC[C@H]6O)nc4cc3Cl)cc2)cc1F]

The title compound is prepared from ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,6-difluorophenyl}imino)dimethyl-$\lambda^6$-sulfanone following a procedure analogous to that described for Example 1. LC (method 2): $t_R$=0.90 min; Mass spectrum (ESI$^+$): m/z=577 [M+H]$^+$.

Example 5

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-3-fluorophenyl}imino)dimethyl-$\lambda^6$-sulfanone

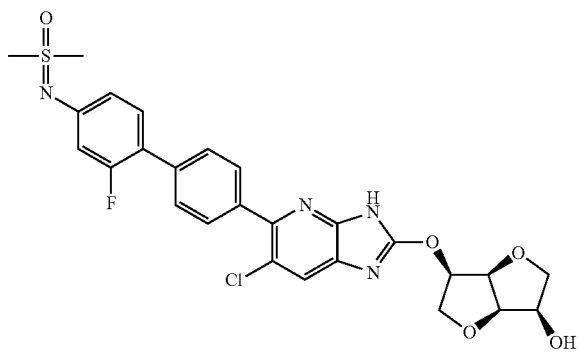 [SMILES: CS(C)(=O)=Nc1ccc(-c2ccc(-c3nc4[nH]c(O[C@@H]5CO[C@H]6[C@@H]5OC[C@H]6O)nc4cc3Cl)cc2)c(F)c1]

The title compound is prepared from ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3-fluorophenyl}imino)dimethyl-$\lambda^6$-sulfanone following a procedure analogous to that described for Example 1. LC (method 2): $t_R$=0.89 min; Mass spectrum (ESI$^+$): m/z=559 [M+H]$^+$.

Example 6

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-2,3-difluorophenyl}imino)dimethyl-$\lambda^6$-sulfanone

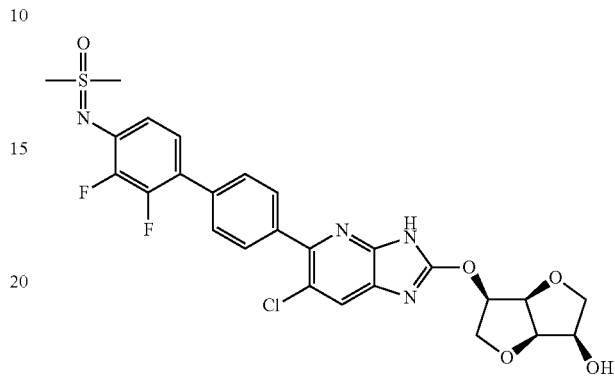

The title compound is prepared from ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-2,3-difluorophenyl}imino)dimethyl-$\lambda^6$-sulfanone following a procedure analogous to that described for Example 1. LC (method 2): $t_R$=0.91 min; Mass spectrum (ESI$^+$): m/z=577 [M+H]$^+$.

Example 7

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)-3-fluorophenyl]phenyl}imino)dimethyl-$\lambda^6$-sulfanone

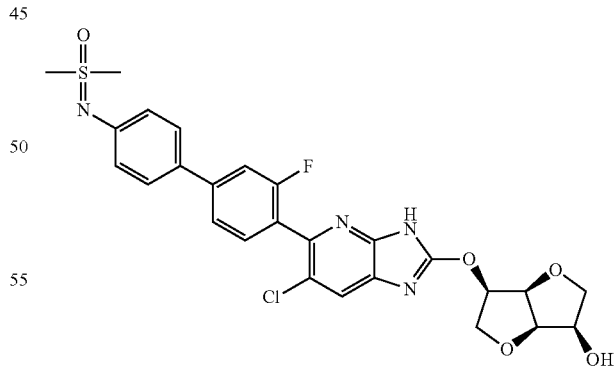

The title compound is prepared from ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}imidazo[4,5-b]pyridin-5-yl)-3-fluorophenyl]phenyl}imino)dimethyl-$\lambda^6$-sulfanone following a procedure analogous to that described for Example 1. LC (method 2): $t_R$=0.88 min; Mass spectrum (ESI$^+$): m/z=559 [M+H]$^+$.

Example 8

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)-2-fluorophenyl]phenyl}imino)dimethyl-$\lambda^6$-sulfanone

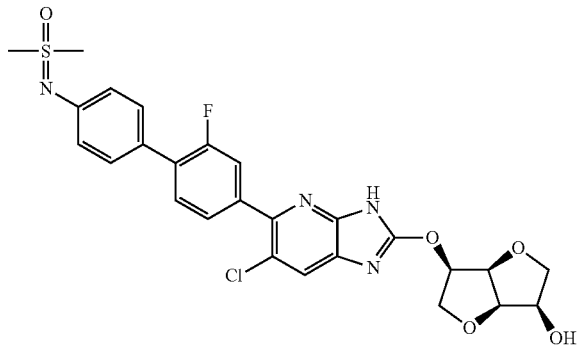 [SMILES: CS(C)(=O)=Nc1ccc(-c2ccc(-c3nc4[nH]c(O[C@@H]5CO[C@H]6[C@@H]5OC[C@H]6O)nc4cc3Cl)cc2F)cc1]

The title compound is prepared from ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}imidazo[4,5-b]pyridin-5-yl)-2-fluorophenyl]phenyl}imino)dimethyl-$\lambda^6$-sulfanone following a procedure analogous to that described for Example 1. LC (method 2): $t_R$=0.89 min; Mass spectrum (ESI⁺): m/z=559 [M+H]⁺.

Example 9

({4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)-2,3-difluorophenyl]phenyl}imino)dimethyl-$\lambda^6$-sulfanone

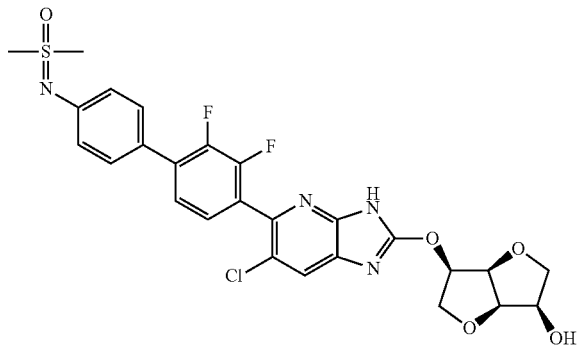 [SMILES: CS(C)(=O)=Nc1ccc(-c2ccc(-c3nc4[nH]c(O[C@@H]5CO[C@H]6[C@@H]5OC[C@H]6O)nc4cc3Cl)c(F)c2F)cc1]

The title compound is prepared from ({4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}imidazo[4,5-b]pyridin-5-yl)-2,3-difluorophenyl]phenyl}imino)dimethyl-$\lambda^6$-sulfanone following a procedure analogous to that described for Example 1. LC (method 2): $t_R$=0.90 min; Mass spectrum (ESI⁺): m/z=577 [M+H]⁺.

Example 10

({6-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-5-fluoropyridin-3-yl}imino)dimethyl-$\lambda^6$-sulfanone

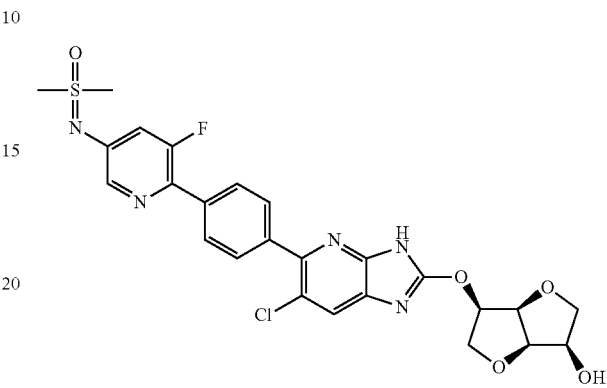

The title compound is prepared from ({6-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-5-fluoropyridin-3-yl}imino)dimethyl-$\lambda^6$-sulfanone following a procedure analogous to that described for Example 1. LC (method 4): $t_R$=0.94 min; Mass spectrum (ESI⁺): m/z=560 [M+H]⁺.

Example 11

({4-[5-(2-{[(3R,3aR,6R,6aR)-6-Hydroxy-hexahydrofuro[3,2-b]furan-3-yl]oxy}-6-chloro-3H-imidazo[4,5-b]pyridin-5-yl)-6-methoxypyridin-2-yl]phenyl}imino)dimethyl-$\lambda^6$-sulfanone

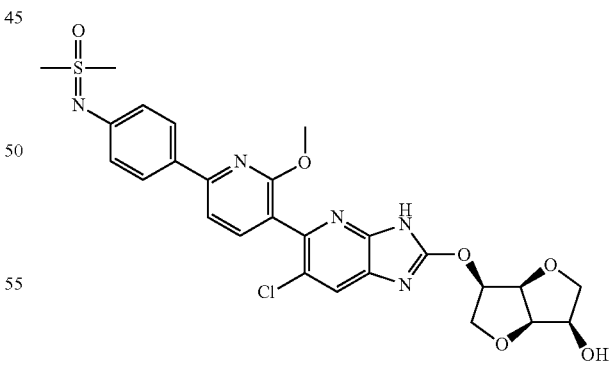

The title compound is prepared from ({4-[5-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)-6-methoxypyridin-2-yl]phenyl}imino)dimethyl-$\lambda^6$-sulfanone following a procedure analogous to that described for Example 1. LC (method 2): $t_R$=0.87 min; Mass spectrum (ESI⁺): m/z=572 [M+H]⁺.

Example 12

({4-[4-(2-{[(3R,3aR,6R,6aR)-6-Hydroxy-hexahydrofuro[3,2-b]furan-3-yl]oxy}-6-fluoro-1H-imidazo[4,5-b]pyridin-5-yl)phenyl]phenyl}imino)dimethyl-$\lambda^6$-sulfanone

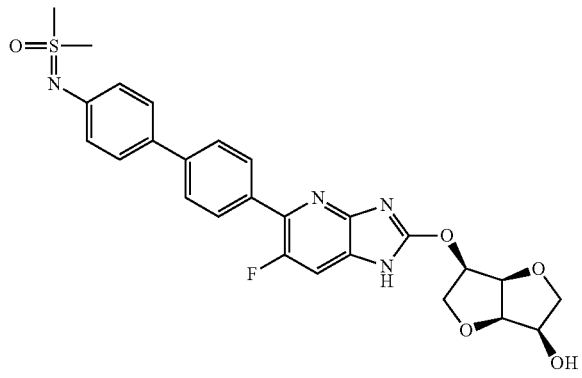 [SMILES: CS(C)(=O)=Nc1ccc(-c2ccc(-c3nc4nc(O[C@@H]5CO[C@H]6[C@@H]5OC[C@H]6O)[nH]c4cc3F)cc2)cc1]

Trifluoroacetic acid (0.57 mL) is added to ({4-[4-(2-{[(3R,3aR,6R,6aR)-6-hydroxy-hexahydrofuro[3,2-b]furan-3-yl]oxy}-6-fluoro-1-{[2-(trimethylsilyl)ethoxy]methyl}-1H-imidazo[4,5-b]pyridin-5-yl)phenyl]phenyl}imino)dimethyl-$\lambda^6$-sulfanone (96 mg) in dichloromethane (5 mL) and the resulting mixture is stirred at room temperature for 28 h. The reaction mixture is concentrated in vacuo and the residue is dissolved in ethyl acetate and methanol. The solution is washed with a saturated aqueous solution of NaHCO$_3$ and brine, dried over MgSO$_4$, and concentrated in vacuo. The residue is triturated with a small amount of methanol, filtered off, and dried to give the title compound. LC (method 1): $t_R$=0.81 min; Mass spectrum (ESI$^+$): m/z=525 [M+H]$^+$.

Example 13

{4-[4-(2-{[(3R,3aR,6R,6aR)-6-Hydroxy-hexahydrofuro[3,2-b]furan-3-yl]oxy}-6-chloro-3H-imidazo[4,5-b]pyridin-5-yl)phenyl]-3-fluorophenyl}(imino)methyl-$\lambda^6$-sulfanone

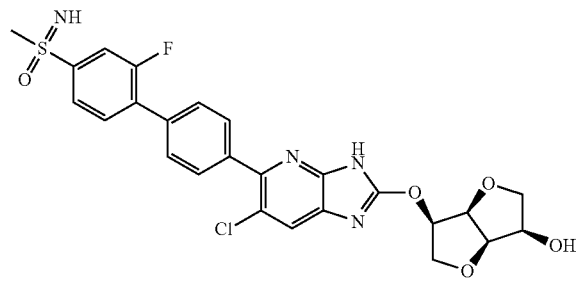 [SMILES: CS(=N)(=O)c1ccc(-c2ccc(-c3nc4[nH]c(O[C@@H]5CO[C@H]6[C@@H]5OC[C@H]6O)nc4cc3Cl)cc2)c(F)c1]

The title compound is prepared from {4-[4-(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)phenyl]-3-fluorophenyl}(imino)methyl-$\lambda^6$-sulfanone following a procedure analogous to that described for Example 1. LC (method 2): $t_R$=0.83 min; Mass spectrum (ESI$^+$): m/z=545 [M+H]$^+$.

Example 14

({4-[4-(2-{[(3R,3aR,6R,6aR)-6-Hydroxy-hexahydrofuro[3,2-b]furan-3-yl]oxy}-6-fluoro-1H-imidazo[4,5-b]pyridin-5-yl)phenyl]-3-fluorophenyl}imino)dimethyl-$\lambda^6$-sulfanone

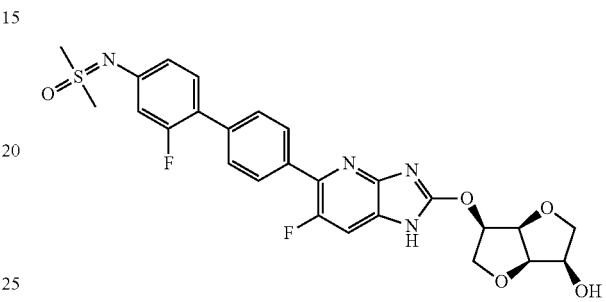

The title compound is prepared from ({4-[4-(2-{[(3R,3aR,6R,6aR)-6-hydroxy-hexahydrofuro[3,2-b]furan-3-yl]oxy}-6-fluoro-1-{[2-(trimethylsilyl)ethoxy]methyl}-1H-imidazo[4,5-b]pyridin-5-yl)phenyl]-3-fluorophenyl}imino)dimethyl-$\lambda^6$-sulfanone following a procedure analogous to that described for Example 1. LC (method 2): $t_R$=0.88 min; Mass spectrum (ESI$^+$): m/z=543 [M+H]$^+$.

Example 15

({4-[5-(2-{[(3R,3aR,6R,6aR)-6-Hydroxy-hexahydrofuro[3,2-b]furan-3-yl]oxy}-6-chloro-3H-imidazo[4,5-b]pyridin-5-yl)-6-methoxypyridin-2-yl]-3-fluorophenyl}imino)dimethyl-$\lambda^6$-sulfanone

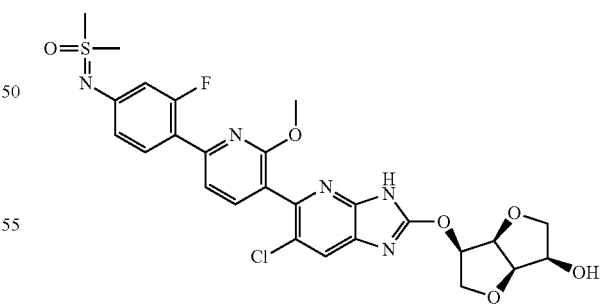

The title compound is prepared from ({4-[5-(2-{[(3R,3aR,6R,6aR)-6-hydroxy-hexahydrofuro[3,2-b]furan-3-yl]oxy}-6-chloro-3H-imidazo[4,5-b]pyridin-5-yl)-6-methoxypyridin-2-yl]-3-fluorophenyl}imino)dimethyl-$\lambda^6$-sulfanone following a procedure analogous to that described for Example 1. LC (method 2): $t_R$=0.90 min; Mass spectrum (ESI$^+$): m/z=590 [M+H]$^+$.

Example 16

({4-[4-(2-{[(3R,3aR,6R,6aR)-6-Hydroxy-hexahydrofuro[3,2-b]furan-3-yl]oxy}-6-fluoro-1H-imidazo[4,5-b]pyridin-5-yl)-3,5-difluorophenyl]phenyl}imino)dimethyl-$\lambda^6$-sulfanone

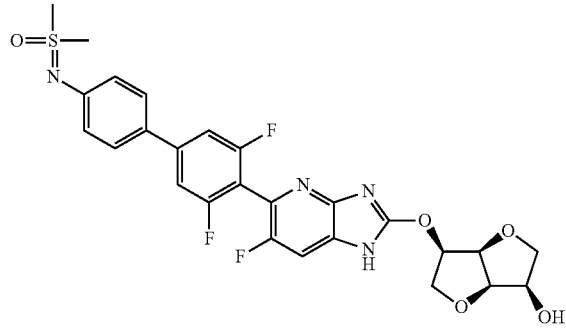 [SMILES: CS(C)(=O)=Nc1ccc(-c2cc(F)c(-c3nc4nc(O[C@@H]5CO[C@H]6[C@@H]5OC[C@H]6O)[nH]c4cc3F)c(F)c2)cc1]

The title compound is prepared from ({4-[4-(2-{[(3R,3aR,6R,6aS)-6-[(tert-butyldimethylsilyl)oxy]-hexahydrofuro[3,2-b]furan-3-yl]oxy}-6-fluoro-3-{[2-(trimethyl-silyl)ethoxy]methyl}imidazo[4,5-b]pyridin-5-yl)-3,5-difluorophenyl]phenyl}imino)dimethyl-$\lambda^6$-sulfanone following a procedure analogous to that described for Example 12. LC (method 2): $t_R$=0.87 min; Mass spectrum (ESI$^+$): m/z=561 [M+H]$^+$.

Example 17

({4-[4-(2-{[(3R,3aR,6R,6aR)-6-Hydroxy-hexahydrofuro[3,2-b]furan-3-yl]oxy}-6-chloro-1H-imidazo[4,5-b]pyridin-5-yl)-3,5-difluorophenyl]phenyl}imino)dimethyl-$\lambda^6$-sulfanone

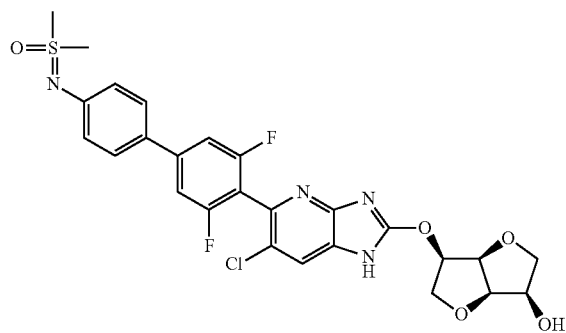 [SMILES: CS(C)(=O)=Nc1ccc(-c2cc(F)c(-c3nc4nc(O[C@@H]5CO[C@H]6[C@@H]5OC[C@H]6O)[nH]c4cc3Cl)c(F)c2)cc1]

The title compound is prepared from ({4-[4-(2-{[(3R,3aR,6R,6aS)-6-[(tert-butyldimethylsilyl)oxy]-hexahydrofuro[3,2-b]furan-3-yl]oxy}-6-chloro-3-{[2-(trimethyl-silyl)ethoxy]methyl}imidazo[4,5-b]pyridin-5-yl)-3,5-difluorophenyl]phenyl}imino)dimethyl-$\lambda^6$-sulfanone following a procedure analogous to that described for Example 1. LC (method 2): $t_R$=0.89 min; Mass spectrum (ESI$^+$): m/z=577 [M+H]$^+$.

The invention claimed is:

1. A compound of formula I containing three (consecutive) aromatic or heteroaromatic moieties

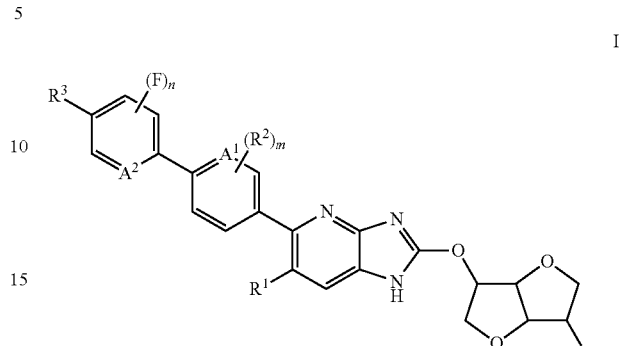

wherein $A^1$ is selected from the group consisting of CH, $CR^2$ and N, $A^2$ is selected from the group consisting of CH, CF and N, $R^1$ is selected from the group consisting of F and Cl, $R^2$ is selected from the group consisting of F and methoxy, $R^3$ is selected from the group consisting of

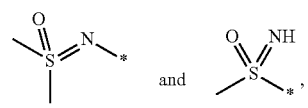

m is selected from an integer consisting of 0, 1 and 2, and n is selected from an integer consisting of 0, 1, and 2, with the provisos, that at least one substituent attached to an aromatic or heteroaromatic moiety in formula I represents F or that $R^2$ represents methoxy, or a salt thereof.

2. A compound according to claim 1 with the substructure of formula II containing a biphenylyl-azabenzimidazole moiety

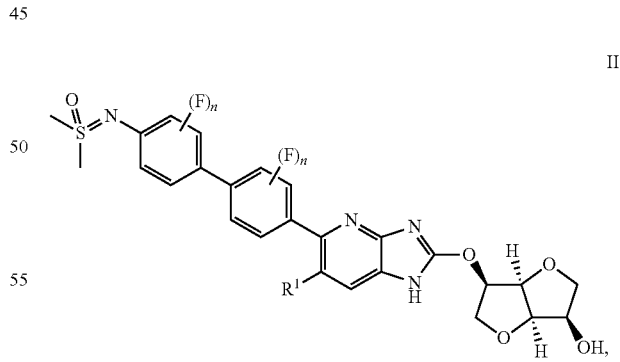

wherein $R^1$ is selected from the group consisting of F and Cl, m is selected from an integer consisting of 0, 1 and 2, and n is selected from an integer consisting of 0, 1, and 2, with the proviso, that at least one substituent attached to the biphenylyl-azabenzimidazole moiety represents F, or a salt thereof.

3. A compound according to claim 1 with the substructure of formula III containing a biphenylyl-azabenzimidazole moiety

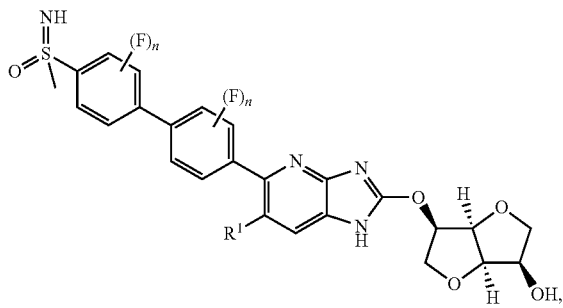

III wherein
R¹ is selected from the group consisting of F and Cl,
m is selected from an integer consisting of 0, 1 and 2, and
n is selected from an integer consisting of 0, 1, and 2,
with the proviso, that at least one substituent attached to the biphenylyl-azabenzimidazole moiety represents F,
or a salt thereof.

4. A compound according to claim 1 with the substructure of formula IV

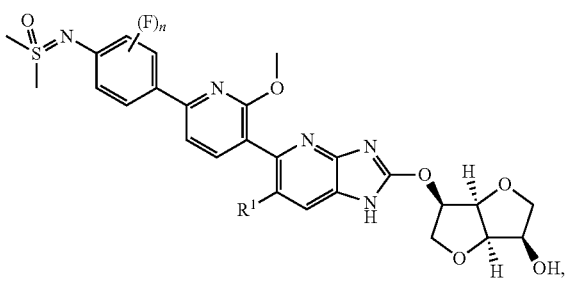

IV wherein
R¹ is selected from the group consisting of F and Cl, and
n is selected from an integer consisting of 0, 1, and 2,
or a salt thereof.

5. A compound according to claim 1 with the substructure of formula V

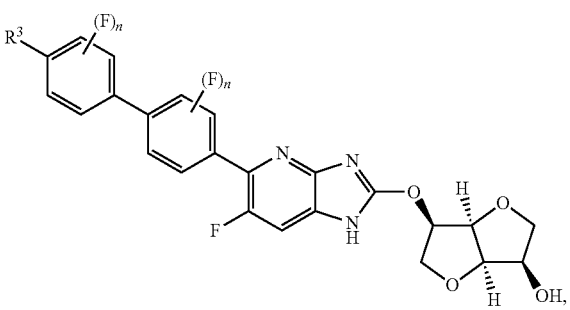

V wherein
R³ is selected from the group consisting of

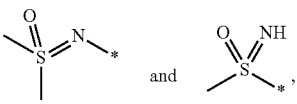

and m is selected from an integer consisting of 0, 1 and 2, and
n is selected from an integer consisting of 0, 1, and 2,
or a salt thereof.

6. A compound according to claim 1 with the substructure of formula VI

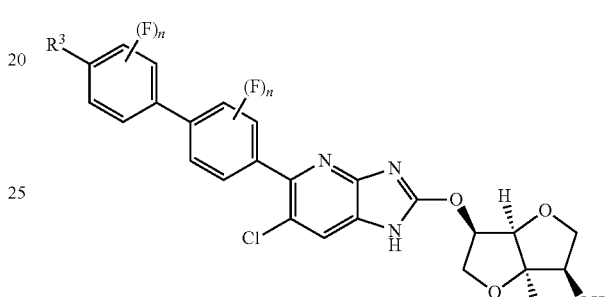

VI wherein
R³ is selected from the group R³-G1 consisting of

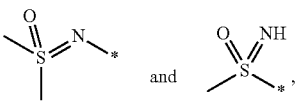

and m is selected from an integer consisting of 0, 1 and 2, and
n is selected from an integer consisting of 0, 1, and 2,
with the proviso, that at least one of m and n denotes 1 or 2,
or a salt thereof.

7. A pharmaceutically acceptable salt of a compound according to claim 1.

8. A pharmaceutical composition comprising one or more compounds according to claim 1 or one or more pharmaceutically acceptable salts thereof, optionally together with one or more inert carriers and/or diluents.

9. A method for treating diseases or conditions which can be influenced by the modulation of the function of AMP-activated protein kinase (AMPK), comprising administering a compound according to claim 1 or a pharmaceutically acceptable salt thereof to a patient in need thereof, wherein the disease or condition is type 2 diabetes mellitus, insulin resistance, obesity, cardiovascular disease, or dyslipidemia.

10. A pharmaceutical composition comprising one or more compounds according to claim 1 or one or more pharmaceutically acceptable salts thereof and one or more additional therapeutic agents, optionally together with one or more inert carriers and/or diluents.

11. The pharmaceutical composition according to claim 10, wherein the one or more additional therapeutic agents is selected from the group consisting of antidiabetic agents, agents for the treatment of overweight and/or obesity and agents for the treatment of high blood pressure, heart failure and/or atherosclerosis.

* * * * *